(12) United States Patent
Chu et al.

(10) Patent No.: US 12,286,627 B1
(45) Date of Patent: Apr. 29, 2025

(54) METHOD FOR PREVENTING dsRNA BACTERIAL SOLUTIONS FROM BEING DEGRADED BY UV LIGHT AND APPLICATION THEREOF IN CONTROL OF SILVERLEAF WHITEFLIES

(71) Applicant: QINGDAO AGRICULTURAL UNIVERSITY, Qingdao (CN)

(72) Inventors: Dong Chu, Qingdao (CN); Zhishao Cen, Qingdao (CN); Lili Wang, Qingdao (CN); Xinxi Ren, Qingdao (CN); Yunli Tao, Qingdao (CN)

(73) Assignee: QINGDAO AGRICULTURAL UNIVERSITY, Shandong (CN)

( * ) Notice: Subject to any disclaimer, the term of this patent is extended or adjusted under 35 U.S.C. 154(b) by 0 days.

(21) Appl. No.: 18/930,307

(22) Filed: Oct. 29, 2024

(30) Foreign Application Priority Data

Dec. 22, 2023   (CN) .......................... 202311774881.8

(51) Int. Cl.
*C12N 15/113*     (2010.01)
*C12Q 1/6806*     (2018.01)

(52) U.S. Cl.
CPC .......... *C12N 15/113* (2013.01); *C12Q 1/6806* (2013.01); *C12N 2310/14* (2013.01)

(58) Field of Classification Search
CPC . C12N 15/113; C12N 2310/14; C12Q 1/6806
USPC ..................... 435/6.1, 91.1, 91.31, 566, 568; 514/44 A, 44 R; 536/23.1, 24.5
See application file for complete search history.

(56) References Cited

U.S. PATENT DOCUMENTS

2006/0272049 A1   11/2006   Waterhouse et al.
2022/0220494 A1   7/2022    Maori et al.

FOREIGN PATENT DOCUMENTS

| CN | 110583581 A | 12/2019 |
| CN | 116445485 A | 7/2023 |
| CN | 116732042 A | 9/2023 |
| CN | 116949051 A | 10/2023 |

*Primary Examiner* — Jane J Zara
(74) *Attorney, Agent, or Firm* — SZDC Law PC

(57) ABSTRACT

The present invention discloses a method for preventing dsRNA bacterial solutions from being degraded by UV light and application thereof in control of silverleaf whiteflies which relates to technical field of pest control. The method for preventing dsRNA bacterial solutions from being degraded by UV light of present invention is to mix dsRNA bacterial solutions with nanomaterial solutions to prepare mixed solutions of nanomaterial as well as dsRNA bacterial solutions, wherein the nanomaterial is one of MON, $Fe_3O_4$, TiC and SiC. Nanomaterials are used to protect dsRNA bacterial solutions from being degraded by UV light, so that lethal effect of dsGawky on silverleaf whiteflies can achieve purpose of pest control. The method is easy to operate, low in cost, good in effectiveness as well as sensitivity, high in insecticidal efficiency, and has other advantages such as environmental friendliness as well as good application prospects.

6 Claims, 13 Drawing Sheets
Specification includes a Sequence Listing.

METHOD FOR PREVENTING dsRNA BACTERIAL SOLUTIONS FROM BEING DEGRADED BY UV LIGHT AND APPLICATION THEREOF IN CONTROL OF SILVERLEAF WHITEFLIES

This application claims priority to Chinese patent application no. 202311774881.8, filed on Dec. 22, 2023, which is incorporated by reference for all purposes as if fully set forth herein.

A sequence listing xml file named "10037_0040.xml" created on Oct. 29, 2024, and having a size of 8,300 bytes, is filed concurrently with the specification. the sequence listing contained in the xml file is part of the specification and is herein incorporated by reference in its entirety.

TECHNICAL FIELD

The present invention relates to the technical field of pest control and relates to the method for preventing dsRNA bacterial solutions from being degraded by UV light and application thereof in control of silverleaf whiteflies.

TECHNICAL BACKGROUND

Silverleaf whiteflies of the species complex of *Bemisia tabaci* (Gennadius) are agricultural pests with the worldwide distribution, belonging to the family Aleyrodidae in the order Hemiptera of the class Insecta. It was firstly discovered on the tobacco in Greece in 1889, and has since been discovered all over world, gradually becoming a super pest worldwide. The main damage caused by this insect mainly includes directly sucking the plant sap, spreading plant viruses and secreting honeydew which causes the sooty mold disease. According to reports, its traces have already been discovered on the remaining six continents except Antarctica, causing billions of dollars annually in economic losses and making it a major global pest. Due to its strong invasiveness, the silverleaf whiteflies are listed as quarantine invasive pest in many countries and regions.

At present, chemical control is the main method for controlling silverleaf whiteflies. Since the silverleaf whiteflies are small sap-sucking insects, its entire development process includes egg, nymph and adult stages. Traditional contact insecticides such as bifenthrin and avermectin can kill adult silverleaf whiteflies quiet well but cannot effectively kill eggs and nymphs of it on the back of leaves. The neonicotinoid insecticides such as imidacloprid as well as thiamethoxam have good plant systemic properties. By spraying and irrigating crops, it can not only kill the adult silverleaf whiteflies, but also effectively kill the nymphs of silverleaf whiteflies, thus can be used as the first choice of drugs for control of the sap-sucking pests. However, with widespread and long-term use of insecticides, resistance has been gradually formed. The research on the mechanism of resistance is an important guarantee for rational use of insecticides and is also regarded as indispensable part of safe and efficient agricultural production.

RNA interference (RNAi) is a mechanism of action that can be triggered by the short RNA-fragments (siRNAs) to promote degradation of homologous mRNA or inhibit its translation. RNAi was first discovered in the nematodes and can function in most organisms. RNAi has been widely used as a tool to study functional genomics and has shown enormous potential in development of new strategies in pest control. Since RNAi technology can specifically inhibit the gene expression, it can efficiently target and silence pest genes, thereby achieving the purpose of pest control.

When the RNA interference fragments are sprayed directly on the surface of plants, it can be directly ingested or absorbed by the pests. However, directly sprayed dsRNA bacterial solutions can be degraded by the nucleases and UV light when exposed to air, resulting in inability to trigger effective RNAi reaction, thereby affecting interference efficiency of the dsRNA bacterial solutions on pests. Research on strategies to prevent dsRNA bacterial solutions from being degraded by UV rays can lay the foundation for application of RNA interference in biological control of pests.

SUMMARY OF THE INVENTION

In view of problems existing in prior art, the objective of present invention is to provide the method for preventing the dsRNA bacterial solutions from being degraded by the UV light and application thereof in control of silverleaf whiteflies.

To achieve the above objective, the technical solution adopted by the present invention is as follows:

The method for preventing dsRNA bacterial solutions from being degraded by UV light comprising mixing the dsRNA bacterial solutions with the nanomaterial solutions to prepare mixed solutions of the nanomaterial and the dsRNA bacterial solutions, wherein the nanomaterial is one of mesoporous organosilica (MON), $Fe_3O_4$, titanium carbide (TiC) and silicon carbide (SiC).

In a specific embodiment, the preparation method of MON is as follows:

1) Under continuous stirring, 0.80 g of cetyltrimethylammonium bromide (CTAB) is dispersed in 384 mL of water to prepare CTAB solutions as aqueous phase.

2) 2.8 mL of 2 mol/L NaOH solutions are added to the CTAB solutions, heated to 80° C. in oil bath, and then 5.6 mL of tetraethyl orthosilicate (TEOS), 12 mL of ethyl acetate, and 0.56 mL of 95% N-2-aminoethyl-3-aminotrimethoxysilane are added dropwise in sequence. Mixed solutions are subsequently stirred at 600 rpm and kept at 80° C. for 3 hours until the solutions become homogeneous.

3) After reaction is completed, obtained crude product is collected through centrifugation at 12000 rpm for 5 min, then washed 3 times with water and ethanol, and then dispersed in 320 mL of ethanol. To remove the free TEOS and CTAB, 320 μL of saturated HCl is added to the particle suspension with the continuous stirring at 70° C. After 8 hours, formed mesoporous silica nanoparticles (MSN) is collected after the centrifugation at 12000 rpm for 5 min, then washed 3 times with ethanol, and then dried at 80° C. for 6 hours.

4) 1.0 g of MSN is ultrasonically dispersed in 150 mL of toluene, heated to 80° C. and stirred for 30 min, then 1.06 mL of 3-(triethoxysilyl)propylsuccinic anhydride (TEPSA) is added and reacted for 24 hours under nitrogen protection.

5) After the reaction is completed, precipitate is collected by centrifugation at 12000 rpm for 5 min, washed 3 times with acetone and dried under vacuum for later use to obtain the MON—COOH.

6) 50 mM of sodium carbonate-carbonate buffer solutions with pH value of 9.6 is prepared, 100 mg of MON—COOH is ultrasonically dispersed in 50 mL of sodium carbonate-carbonate buffer solutions, another 50 mL of sodium carbonate-carbonate buffer solutions containing 100 mg of PEI is prepared and added to the sodium carbonate-carbonate buffer solutions in which MON—COOH is dispersed, and 57.51 mg of 1-ethyl-3-(3-dimethylaminopropyl)carbodiimide (EDC) as well as 34.527 mg of NHS are added thereto. After these two materials are prepared into solutions with the final concentration of 3 mM, the solutions are stirred at the room temperature for 4 hours. After the reaction is completed, the solutions are collected by centrifugation at 12000 rpm for 5 min, washed 3 times with pure water, and then vacuum-dried for later use which is recorded as MON.

The above method for preventing the dsRNA bacterial solutions from being degraded by UV light is applied in RNA interference to control agricultural pests.

The biological agent for controlling silverleaf whiteflies, comprising nanomaterial as well as dsRNA bacterial solutions interfering with the Gawky gene of the silverleaf whiteflies, wherein nanomaterial is one of MON, $Fe_3O_4$, TiC and SiC.

In a specific embodiment, the dsRNA bacterial solutions interfering with the Gawky gene of silverleaf whiteflies are bacterial solutions that transcribe dsRNA of Gawky gene of silverleaf whiteflies.

In a specific embodiment, the bacterial solutions transcribing dsRNA of the Gawky gene of silverleaf whiteflies are prepared by the following method:

using primers to amplify the dsRNA sequence of Gawky gene, connecting it to expression vector, constructing recombinant vector, and transforming expression strain; inducing expression strain to transcribe dsRNA sequence of Gawky gene, discarding supernatant solutions in bacterial solutions, and dissolving as well as diluting it with $ddH_2O$ to obtain the results.

In a specific embodiment, the method for inducing expression strain to transcribe dsRNA sequence of Gawky gene is as follows:

inoculating the recombinant bacteria transformed with the recombinant vector expressing dsRNA of Gawky gene of silverleaf whiteflies into LB medium containing Amp, culturing at 37° C. with shaking at 20 r/min, and when the OD600 value of bacterial solutions reaches 0.5, adding isopropyl-β-D-Thiogalactoside (IPTG) solutions with final concentration of 0.5M to induce for 4 hours to obtain the results.

The preparation method of the above biological agent for controlling silverleaf whiteflies comprises the following steps:

1) Preparing nanomaterial into aqueous solutions with identical concentration as bacterial solutions transcribing dsRNA of Gawky gene of silverleaf whiteflies.

2) Mixing aqueous solutions of nanomaterial with bacterial solutions transcribing dsRNA of Gawky gene of silverleaf whiteflies at a volume ratio of 6:1, and shaking as well as mixing for 30 minutes to obtain mixed solutions of nanomaterial and bacterial solutions transcribing dsRNA of Gawky gene of silverleaf whiteflies used for RNAi interference of silverleaf whiteflies.

The biological agent for controlling silverleaf whiteflies prepared by the above method is applied in biological control of silverleaf whiteflies.

The method for biological control of silverleaf whiteflies, comprising spraying biological agents prepared by above method on plants for controlling silverleaf whiteflies, so that silverleaf whiteflies feed on plants after spraying, thereby increasing mortality of silverleaf whiteflies.

In a specific embodiment, silverleaf whiteflies are Q-type silverleaf whiteflies or B-type silverleaf whiteflies.

The beneficial effects of technical solutions of the present invention are as follows:

The present invention develops a technology based on nanomaterials that can prevent UV light from degrading the dsRNA bacterial solutions. That is, the aqueous solutions of MON, $Fe_3O_4$, TiC or SiC are shaken as well as mixed with dsRNA bacterial solutions to form the mixed solutions of nanomaterial as well as dsRNA bacterial solutions, and nanomaterial is used to protect dsRNA bacterial solutions from being degraded by UV light, so that lethal effect of dsGawky on silverleaf whiteflies can achieve the purpose of the pest control. The present material can complete effective load of dsRNA bacterial solutions by electrostatic action, and can also improve colloidal stability, biodegradability, biocompatibility as well as stimulus responsiveness at the same time. The present method is simple to operate, low in cost, good in effectiveness and sensitivity, high in insecticidal efficiency, and has other advantages such as environmental friendliness as well as good application prospects.

In addition, the present invention utilizes plasmid L4440 and strains of *Escherichia coli* HT115 (DE3) to synthesize large amount of dsRNA of Gawky gene and utilizes a spraying method to simulate the field use. Compared with the commercialized dsRNA synthesis kits, the method of synthesizing dsRNA with engineering bacteria greatly reduces the synthesis costs of dsRNA. The present method will provide the possibility for large-scale analysis of functions of the insect gene and field use of RNAi agents and is expected to promote practice and development of pest control technology with RNAi as the core and has good application prospects.

DETAILED DESCRIPTION OF THE EMBODIMENTS

Figure 1:
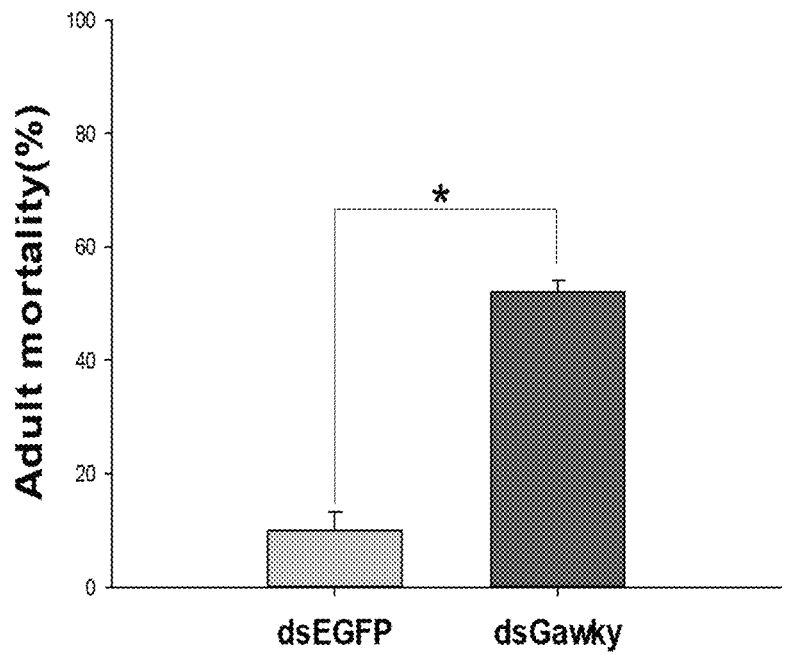
FIG. 1 shows lethal effect of spraying bacterial solutions transcribing dsGawky bacterial cells on the adult Q-type silverleaf whiteflies. (dsEGFP is the control group of spraying bacterial cells transcribing dsEGFP, dsGawky is the treatment group of spraying bacterial cells transcribing dsGawky and "*" indicates a significant difference between the two.)

The terms used in present invention, unless otherwise specified, generally have meanings commonly understood by ordinary technicians in the field.

The present invention is further described in detail below in conjunction with the specific embodiments and with reference to data. The following embodiments are only for the purpose of illustrating present invention and are not intended to limit scope of present invention in any way.

The population of silverleaf whiteflies used in following embodiments was collected from Lingshui City, Hainan Province, P.R.C. in January 2017. These insects were raised in insect-proof cages (temperature 27±1° C., relative humidity 60%±5%, photoperiod 16L:8D) on the variety of common tobacco NC89 for a long period of time.

In the following embodiments, the preparation method of MON was as follows:

1) Under continuous stirring, 0.80 g of CTAB was dispersed in 384 mL of water to prepare CTAB solutions as aqueous phase.

2) 2.8 mL of 2 mol/L NaOH solutions were added to the CTAB solutions, heated to 80° C. in oil bath, and then 5.6 mL of TEOS, 12 mL of ethyl acetate, and 0.56 mL of 95% N-2-aminoethyl-3-aminotrimethoxysilane were added dropwise in sequence. The mixed solutions were then stirred at 600 rpm and kept at 80° C. for 3 hours until the solutions become homogeneous.

3) After reaction was completed, the crude product was collected through centrifugation at 12000 rpm for 5 min, then washed 3 times with water and ethanol, and then dispersed in 320 mL of ethanol. To remove the free TEOS and CTAB, 320 µL of saturated HCl was added to the particle suspension with continuous stirring at 70° C. After 8 hours, the formed MSN was collected after the centrifugation at 12000 rpm for 5 min, then washed 3 times with ethanol, and then dried at 80° C. for 6 hours.

4) 1.0 g of MSN was ultrasonically dispersed in 150 mL of the toluene, heated to 80° C. and stirred for 30 min, then 1.06 mL of the TEPSA was added and reacted for 24 hours under nitrogen protection.

5) After reaction was completed, precipitate was collected by centrifugation at 12000 rpm for 5 min, washed 3 times with acetone and dried under vacuum for later use to obtain the MON—COOH.

6) 50 mM of the sodium carbonate-carbonate buffer solutions with a pH value of 9.6 was prepared, 100 mg of the MON—COOH was ultrasonically dispersed in 50 mL of sodium carbonate-carbonate buffer solutions, another 50 mL of the sodium carbonate-carbonate buffer solutions containing 100 mg of PEI was prepared and added to sodium carbonate-carbonate buffer solutions in which MON—COOH was dispersed, and 57.51 mg of EDC as well as 34.527 mg of NHS were added thereto. After these two materials were prepared into solutions with a final concentration of 3 mM, the solutions were stirred at room temperature for 4 hours. After the reaction was completed, the solutions were collected by centrifugation at 12000 rpm for 5 min, washed 3 times with the pure water, and then vacuum-dried for later use which was recorded as MON.

The nanomaterial $Fe_3O_4$ described in the present invention was manufactured by Jiangsu Xianfeng Nanomaterials Technology Co., Ltd., and nanomaterials TiC, SiC, $MnO_2$, $TiO_2$, $CeO_2$, CuS, $CB_4$, ZrC, $Al_2O_3$, $N_4Si_3$, $Co_3O_4$ and AlN were manufactured by Merck & Co., Inc.

Embodiment 1

A method for preventing dsRNA bacterial solutions from being degraded by the UV light, comprising preparing nanomaterial into aqueous solutions with identical concentration as dsRNA bacterial solutions and mixing aqueous solutions of nanomaterial with dsRNA bacterial solutions at a volume ratio of 6:1.

The nanomaterial was one of MON, $Fe_3O_4$, TiC and SiC.

Embodiment 2

The mixed solutions for RNAi interference of silverleaf whiteflies, preparation method of which was as follows:

1) Preparing nanomaterials MON, $Fe_3O_4$, TiC or SiC into aqueous solutions with identical concentration as dsRNA bacterial solutions of the silverleaf whiteflies.

2) Mixing aqueous solutions of nanomaterials MON, $Fe_3O_4$, TiC or SiC with the dsRNA bacterial solutions of silverleaf whiteflies in a volume ratio of 6:1, and after 30 min of shaking and mixing, mixed solutions of nanomaterials and dsRNA bacterial solutions for RNAi interference of silverleaf whiteflies can be obtained.

Embodiment 3

The method for biological control of the silverleaf whiteflies based on nanomaterial MON had the following steps:

1) Preparing the nanomaterial MON into aqueous solutions with identical concentration (2 g/L) as the solutions of transcribed dsGawky bacterial cells (i.e., the bacterial cells that transcribe dsRNA of Gawky gene of silverleaf whiteflies).

2) Mixing the aqueous solutions of nanomaterial MON with the solutions of transcribed dsGawky bacterial cells in the volume ratio of 6:1, and after 30 min of shaking and mixing, mixed solutions of nanomaterial MON and transcribed dsGawky bacterial cells for RNAi interference of silverleaf whiteflies can be obtained.

3) Spraying the mixed solutions of nanomaterial MON and transcribed dsGawky bacterial cells on plants, so that silverleaf whiteflies fed on sprayed plants, thereby increasing the mortality rate of silverleaf whiteflies.

Solutions of the transcribed dsGawky bacterial cells can be prepared by method described in the Chinese patent application "GAWKY GENE OF THE SILVERLEAF WHITEFLIES AND APPLICATION THEREOF IN BIOLOGICAL CONTROL OF SILVERLEAF WHITEFLIES" with Publication Number CN116732042A which was as follows:

According to the sequence of Gawky gene of the silverleaf whiteflies (SEQ ID NO.1), the primers for dsRNA of Gawky gene were designed as well as prepared, and the PCR amplification was performed using the cDNA reversely transcribed from the total RNA of silverleaf whiteflies as a template. The PCR reaction system was 2.5 μL of the 10× buffer, 2 μL of the dNTP, 1 μL of the upstream primer, 1 μL of the downstream primer, 0.25 μL of the rTaq, 17.25 μL of the $H_2O$ and 1 μL of the cDNA. The reaction procedure was as follows: the pre-denaturation at 90° C. for 15 min, the denaturation at 95° C. for 10 s and the annealing respectively at 60° C. for 30 s as well as at 72° C. for 10 s which were repeated 40 times. After PCR was extended at 72° C. for 10 min, the product was recovered, and the amplified product after the enzyme digestion was connected to linearized L4440 plasmid using T4 DNA ligase and converted into HT115 (DE3) competent state. Finally, 300 μL of it was aspirated and coated on a solid culture medium containing 100 mg/mL of $Amp^+$, and the inverted culturing was carried out at 37° C. overnight. On the next day, single bacterial colonies on 6 plates were randomly picked and dissolved in culture medium to prepare bacterial solutions. The bacterial cells which can be successfully identified by PCR were the target recombinant bacteria.

The above recombinant bacteria were inoculated into 15 mL of LB medium ($Amp^+$) and cultured at 37° C. with shaking at 20 r/min. When the OD value of the bacterial solutions reached 0.5, IPTG solutions with final concentration of 0.5M were added for 4 hours of induction to obtain bacterial solutions of transcribed dsGawky bacterial cells. The bacterial solutions were centrifuged at 4° C. and 5000×g for 10 min to separate bacterial cells and to discard supernatant solutions. Then, the bacterial cells were resuspended and mixed with small amount of PBS solutions. The bacterial solutions were centrifuged at 4° C. and 5000×g for 5 min to discard the supernatant solutions. This procedure was repeated twice. Then the bacterial cells were placed in −20° C. refrigerator and stored for future use.

When in use, $ddH_2O$ was used for dissolution as well as dilution to dilute it into bacterial solutions with wet bacterial concentration of 2 g/L.

```
SEQ ID NO. 1 (5' → 3'):
ATGAACTCTTCTCTCTCCTCCCTCTACAAAATTTCAACTCATTCATTCA

TCAGTGAAGGAGAGATGTCCACGACAGTGAACGCATCTGCCGATCAAAA

TCGGAATCTTCCTACCTACCAAGTGCCTAATAGTAGGGACACAATGAAT

GCGGTAGAAACATCTGCCGTTGCTGTGAGGAATAAAATCAAATCACCGC

ACAGAGCGGAGAGTGATGGAGGCAGAGCTGGCCTCTTTCACTTCCTCCC

TTCGACTGTGATAACCAGCTCATTAACTTGTAGTGGAGATCCGTCCTAC

ACGCTACAGGGCTTGAAAGCAAAAGCTGTCGGTTCAACTGATAGCGATT

GTTGCGATGAAAAAAGAATGATGAGGCAAGAAGCCTTGACCCTAGGATC

GGTTGACATTGGTGCTCAGGATAAGTCTTCTACTACTAATAATTGTTCT

ACTATTAATGATAAGCATAGGATTAAGTCCGTTGATACTACTAGTTGTA

ATGCTAATAATGTGACGACGAACAATGCGGAAAACATTCCTTCAAATGA

GTGGATAGCAATTTTAAATACCACGACAAAGCCTTATTCCTCAGGTGAT

TTACTTCAGGGTAACTCTAAGCTAAATCACCGCTTAACGAATTCCCCGT

TAAACTCCTTTCAAGACTGTGATGTTATTCGAGACTACCACTTGAGGTG

GAACATCCTGCCAACTTGTCGATTGGTGGGTGGTGGGGAGAGTTCGCTT

GCTTCAGCAACCTCCACCAACTCGGGCTGGGGAACGAACAACAACAACT

CAGGATCGAGCGCCCCACCAAGTGGATGGAGTGCACCGACCAATGCTGC

TCAGCCACCACCAACATCGACTGCTTCAGGACCTCCTGCCAACTGGAAT

AGCAGCAACAGCAATTCCCCCAACTCATCCTCGCAATCTCAGTCACAAA

ACCGTCAGCCACCGGCAAATAATGCTAGTCAAGGAACCAATAATCTGCA

AAACAATGCTTCTAAAGCAAACCCAGCGATGAGTACCAGTAGCAACAAT

CAGCGCCAGTCAACTAGCCAGCCACCTCCGGCCACTTCTCAAGCCAATA
```

```
GTACCACATCTTGGGCACAGGCTGCTGGCAAGAACCTTCCCAACGCACC
ACCTACCACAACTCCTGCACCACCCATGACTTCAACAGCATCGACCACC
AACAACAACTCGACGAAGCAACAGTTGGAGCAGCTCAACTCTATGCGTG
AAGCCCTCTTCAGTCAGGATGGTTGGGGAGGACAACATGTGAACCAAGA
CAGTGGTTGGGATGTCTCCCCTTCACCAGAACCAGTTGCTAAAGATCAA
ACCGGTGCAACAGTACCTGCATGGAAGCCAAATATAAATAATGGAACTG
AGCTTTGGGAAGCCAACTTGCGCAGTGGCGGTCAGCCTGCAGCTCCACC
GCAACCCAAAACACCATGGGCCATACTCCCACGACTAATATTGGTGGC
ACGTGGGGCGAAGATGATGATGTCAGTAGCGAAGCGACCAATGTCTGGA
CTGGAGTTCCTCCAAACAATCAACCGCAATGGACAGGCGGCCCCAACAA
TCCCATGTGGCCAGGTGGAGACAAAAAAGGTAGTGAGTGGGGTGGAAAC
AATGCCGGTTGGCCGTATGACCCCTCCCGCGGTCTTGCTCCAAAAGTTG
ATCCAAGAGATCAACATCGTATGGCTGTAGCTGATCACAGAGGCATTGG
TGCTGATGATAGAATTGGTTTGATGAGAGGAGATCCTCGTGGAATAAGT
GGGCGCCTGAATGGAGCTGGTGGTGCTGATCCTGCTATGTGGGTCCTG
CTCCTCCGCCACAACAACCACCAGCTCCCCATCATCCCCGCCTGGACC
ACCTCCTGGACCTGGTCAACCACCCAACAAAATTTTACCACCAGCTCTA
GCTGGCGTAAACCATTGGACTGGTCCCAACTCTAATGATATGAACATGG
CCGCTGGTGGAGGAAAACCCAATGGCTGGGACGAACCCTCTCCACCTGC
TCAAAGACGGAACATGCCAAACATGCCTGGTTATGACGACGGTACAGCT
CTATGGGGAAATCAAGGTAACAATAAAGTCACTCATTGGAAAGAAATGC
CAAATCCTAATATGGCTCATGGAATGCCCGGCCCTGCCATCCCTCAAAA
TAGAATGCCTGGAAATGTTACCAACATGAAACCTGATCCGTCTTCTTGG
GGTCACCCGACTAGAAACGGAGGATGGGCGATGGATCTGCTAACCCTG
GAAGTGGCCCAGACTCAAGCGTGCCTTGGGGTGATGACAAAATTGCGGG
TAACTGGAACGAGCCACCGATACCATCTGGTTGGGCTGGTACGGCTCCG
CCGAAGAATGCACCCGGACCGTGGATTGATGGTGATGTTGACCCATCAA
ATTGGGGCCATCCTCCCAAGCAGGGTCCAAAGCCGTTGACTAAAGATAT
CATTTGGTCTAGCAAGCAGTTCAGAATTCTTGCTGATATGGGTTTCAAG
AAAGATGATATTGAAAACGCATTGCGTGTCAGCAACATGGTTCTGGAAG
ATGCTCTAGAAATGCTGAACCCAGCGCGAAATGTGGGAGGTGCTAATGC
TCCTGATCTCTGGCGTCCCGACGCTGCCGCTCCATTTGACCCAACGCAA
TTCCCTCCCTCTCAGCCTCGCTTTCCGCAGCAGATGCCTTTCGCTCCTC
CGACTGGTGTCGCTCCGTCGGTTCCCCCACCTCCCCATCAGAAGTTGCT
CTCTCAGCCACCGCCATCCACAGCCGGTCAGCAACCACCACATTTCAAT
CAATCTTCAAGAGGAGGGAACTCGAGCTATCAACCGACTCCTCAGCAGC
TTCGTGTTTTGGTTCAGCAAATCACAATGGCAGTTCAAGCTGGGTATCT
TAATCAGCAGATATTGAATCAGCCCTTGGCTCCTCAGACTCTTCTCCTT
TTAAATCAGTTACTTCAACATATCAAGTCGCTTCAACAACTTATCCAGC
AGAGAAATCTACATGCCAGCAGCAACCCTCTTGGGAAGAGCAACAACTC
AGCATTCATGCACCTTACAGCTCAAATCACCAAAACCAAGAAACATATC
GCCGGGCTTCAGAACGACATAGTAATTCAGCAAGCGCAGTATATCAAAA
ACCAGATACCATCACAGCAGCATCAGCAGCAACACCACCTTGCATCAGG
CAATAATCAGTCACAAGGTAATGCAGGTGGTGGAGGTAGCAATGATTTC
TTCAACAAGAATCAAGCACAGGATCTCTTGGCAGCTCTTCAAACCAATT
TCACAGACTTGAACATTAATAAAGAACCATTGTCAAGTGGAGCAGGTTT
CCAACACCAGCAATCACGTTTGAATCAATGGAAGTTACCATCTCTGGAC
AAGGAGGGTGAAGTCGGTGAAGACTTCAGCCGTGCCCCAGGAACCACCT
CTAAATCTGGAGGCTCTACGTCTCCCACATTAAATCCTCTGCTGGGCCC
AGACGGGCCTTGGTCATCAAGTGTTTCGAATGCAAACAGCACTGGTTGG
CCCGATTCTGAGAAAGACTGGCCTTCATCACAGGCCAACTCCTCATCTG
CGTTTACTGACCTTGTGCCTGAGTTTGAGCCTGGAAAACCGTGGAAAGG
CAGTGTATTGAAAAGCATTGAAGATGACCCTAGCATCACCCCTGGATCA
GTCGTACGATCTCCCCTCAGCCTGGCCTCAATCAAAGACTCAGAAATAT
TTAGCTCTAGTAAGACTTCGCCAAACAGCACCAACAACTCCGCCTCTGA
CAACTTACCTCTACCTCCGCTGTCTCTGTCGTCATCAACTTGGAGCTTC
AATCCCTCTTCAACTGCACCTTCTTCTTTTACTGGACCTCTTGCCAAAT
TGGGCACTACTGGTAAAACAACCAGTTGGGGAGATGCTCAGCCACCAAC
TGTAGTTACAAGCGAACTGTGGGGCGCACCGAAATCACGCGGTCCTCCC
CCAGGTCTCTCCTCCAAGACTGGCTCTGCTCAAAACTCAGGTTCAAGTA
GCAATGGCTGGACTGCTGGCTCCAATTGGAGTAGTGGCGCTCATTCCGG
CTCATCCTCTCAGTGGCCCTCATCTTCATCATGGCTTTTACTCCGAAAT
TTGACTGCTCAGATCGATGGTTCAACATTAAAAACGCTTTGTTGTCAAC
ACGGTCCTCTGCAAAACTTCCATTTGTACCTGAAACATGGGATTGCCCT
TGCTAAATACTCAACAAAGAAGAGGCTGTGAAGGCTCAAGGTGCTTTG
AACAATTGCGTGTTAGGGAACACGACAATATTCGCAGAATCTCCGGCCG
AGTCAGAAGTGCATTCATTACTTCAACACCTCGGCCAGCAAGGAGGGTC
CAACAGTGGCTGGAACCGTCCTACGGGGGAGCCCCGAAACCTGCAGGT
ACAACTGATACTTGGAGCTCGGGTTGGCCGTCAAACTCACCTTCAAGTA
GCTTGTGGGGTGCTCCTCCTTTGGACGAGCATCGCTCAACCCCATCTTT
GAATTCTTTCTTACCTGGTGATCTTTTGGGTGGTGAATCAATGTAA
```

The primers for preparing dsRNA of the Gawky gene were as follows:

Forward primer: dsGawkyF (SEQ ID NO. 2)
5'-CGAGCTCGCTTCTTACTCCGTGGCAACC-3'.

Reverse primer: dsGawkyR:

(SEQ ID NO. 3)
5'-CCTCGAGGTGACATCATTGCTCCTGCAT-3'.

Embodiment 4

The method for biological control of the silverleaf whiteflies based on nanomaterial $Fe_3O_4$ had the following steps:

1) Preparing the nanomaterial $Fe_3O_4$ into aqueous solutions with identical concentration (2 g/L) as solutions of transcribed dsGawky bacterial cells.

2) Mixing the aqueous solutions of nanomaterial $Fe_3O_4$ with the solutions of transcribed dsGawky bacterial cells in the volume ratio of 6:1, and after 30 min of shaking and mixing, mixed solutions of nanomaterial $Fe_3O_4$ and transcribed dsGawky bacterial cells for RNAi interference of silverleaf whiteflies can be obtained.

3) Spraying the mixed solutions of nanomaterial $Fe_3O_4$ and transcribed dsGawky bacterial cells on plants, so that silverleaf whiteflies fed on sprayed plants, thereby increasing the mortality rate of silverleaf whiteflies.

Solutions of the transcribed dsGawky bacterial cells can be prepared by method described in the Chinese patent application "GAWKY GENE OF THE SILVERLEAF WHITEFLIES AND APPLICATION THEREOF IN BIOLOGICAL CONTROL OF SILVERLEAF WHITEFLIES" with Publication Number CN116732042A. When in use, $ddH_2O$ was used for dissolution as well as dilution to dilute it into bacterial solutions with wet bacterial concentration of 2 g/L.

Embodiment 5

The method for biological control of the silverleaf whiteflies based on nanomaterial TiC had the following steps:

1) Preparing the nanomaterial TiC into the aqueous solutions with identical concentration (2 g/L) as solutions of transcribed dsGawky bacterial cells.

2) Mixing aqueous solutions of nanomaterial TiC with solutions of transcribed dsGawky bacterial cells in the volume ratio of 6:1, and after 30 min of shaking and mixing, mixed solutions of nanomaterial TiC and transcribed dsGawky bacterial cells for RNAi interference of silverleaf whiteflies can be obtained.

3) Spraying the mixed solutions of nanomaterial TiC and transcribed dsGawky bacterial cells on plants, so that silverleaf whiteflies fed on sprayed plants, thereby increasing the mortality rate of silverleaf whiteflies.

Solutions of transcribed dsGawky bacterial cells can be prepared by method described in the Chinese patent application "GAWKY GENE OF THE SILVERLEAF WHITEFLIES AND APPLICATION THEREOF IN BIOLOGICAL CONTROL OF SILVERLEAF WHITEFLIES" with Publication Number CN116732042A. When in use, $ddH_2O$ was used for dissolution as well as dilution to dilute it into bacterial solutions with wet bacterial concentration of 2 g/L.

Embodiment 6

The method for biological control of the silverleaf whiteflies based on nanomaterial SiC had the following steps:

1) Preparing nanomaterial SiC into aqueous solutions with identical concentration (2 g/L) as solutions of transcribed dsGawky bacterial cells.

2) Mixing aqueous solutions of nanomaterial SiC with solutions of transcribed dsGawky bacterial cells in the volume ratio of 6:1, and after 30 min of shaking and mixing, mixed solutions of nanomaterial SiC and transcribed dsGawky bacterial cells for RNAi interference of silverleaf whiteflies can be obtained.

3) Spraying the mixed solutions of nanomaterial SiC and transcribed dsGawky bacterial cells on plants, so that silverleaf whiteflies fed on sprayed plants, thereby increasing the mortality rate of silverleaf whiteflies.

Solutions of transcribed dsGawky bacterial cells can be prepared by method described in the Chinese patent application "GAWKY GENE OF THE SILVERLEAF WHITEFLIES AND APPLICATION THEREOF IN BIOLOGICAL CONTROL OF SILVERLEAF WHITEFLIES" with Publication Number CN116732042A. When in use, $ddH_2O$ was used for dissolution as well as dilution to dilute it into bacterial solutions with wet bacterial concentration of 2 g/L.

Embodiment 7

The following was the lethal effect of spraying bacterial solutions of transcribed dsGawky bacterial cells on adult Q-type silverleaf whiteflies.

The bacterial solutions of transcribed dsGawky bacterial cells prepared in Embodiment 3 were dissolved and diluted with $ddH_2O$ to dilute it into the bacterial solutions with wet bacterial concentration of 2 g/L, and then sprayed on cotton plants, spraying 3 times on the front and back of cotton leaves. After solutions were dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed in an incubator with no sunlight, with a temperature of 27±1° C., with relative humidity of 60%±5%, and with photoperiod of 16L:8D. The identical spraying was carried out with dsEGFP as the control. The results of adult mortality after 2 days of spraying were shown in FIG. 1 which shows that mortality of the adults sprayed with dsGawky bacterial solutions (52%) was significantly increased compared with the control.

Embodiment 8

The following was lethal effect of spraying mixed solutions of nanomaterial MON and transcribed dsGawky bacterial cells on adult Q-type silverleaf whiteflies.

Figure 2:
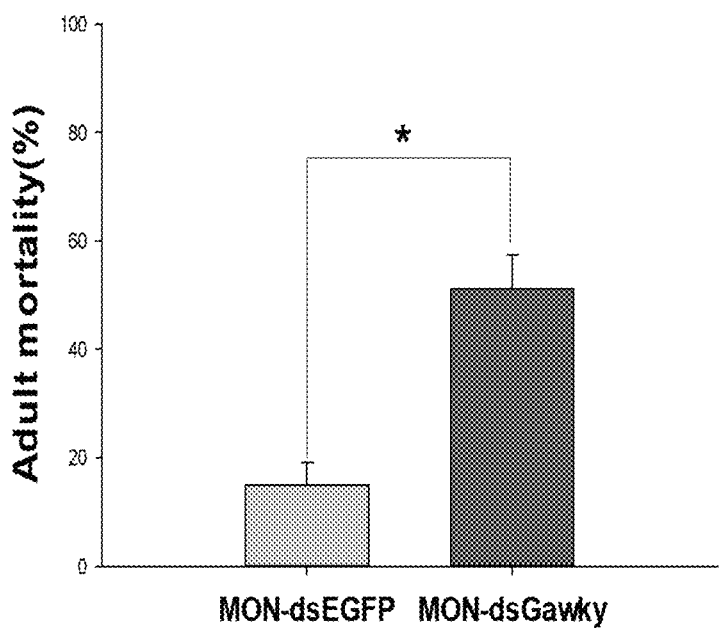
FIG. 2 shows the lethal effect of spraying the mixed solutions of nanomaterial MON and transcribed dsGawky bacterial cells on the adult Q-type silverleaf whiteflies. (MON-dsEGFP is control group of spraying mixed solutions of nanomaterial MON and transcribed dsEGFP bacterial cells, MON-dsGawky is treatment group of spraying mixed solutions of nanomaterial MON and transcribed dsGawky bacterial cells and "*" indicates a significant difference between the two.)

The mixed solutions of nanomaterial MON as well as transcribed dsGawky bacterial cells prepared in Embodiment 3 were sprayed on the cotton plants, spraying 3 times on front and back of cotton leaves. After solutions were dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed in an incubator with no sunlight, with a temperature of 27±1° C., with relative humidity of 60%±5%, and with photoperiod of 16L:8D. The identical spraying was carried out with dsEGFP as the control. The results of adult mortality after 2 days of spraying were shown in FIG. 2 which shows that mortality of the adults sprayed with dsGawky bacterial solutions (51%) was significantly increased compared with the control.

Embodiment 9

The following was lethal effect of spraying mixed solutions of nanomaterial $Fe_3O_4$ and transcribed dsGawky bacterial cells on adult Q-type silverleaf whiteflies.

Figure 3:
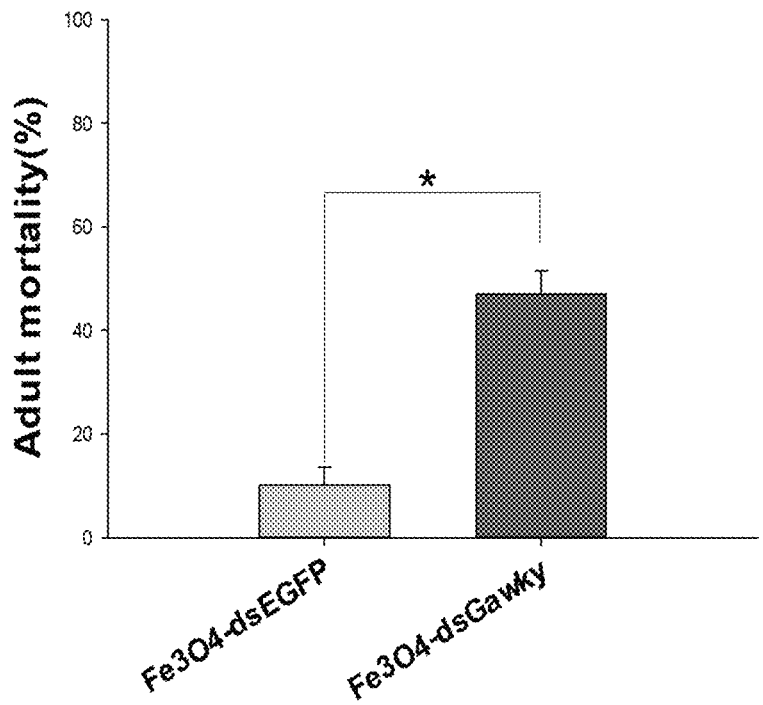
FIG. 3 shows the lethal effect of spraying the mixed solutions of nanomaterial $Fe_3O_4$ and transcribed dsGawky bacterial cells on the adult Q-type silverleaf whiteflies. ($Fe_3O_4$-dsEGFP is control group of spraying mixed solutions of nanomaterial $Fe_3O_4$ and transcribed dsEGFP bacterial cells, $Fe_3O_4$-dsGawky is treatment group of spraying mixed solutions of nanomaterial $Fe_3O_4$ and transcribed dsGawky bacterial cells and "*" indicates a significant difference between the two.)

The mixed solutions of nanomaterial $Fe_3O_4$ as well as transcribed dsGawky bacterial cells prepared in Embodiment 2 were sprayed on the cotton plants, spraying 3 times on front and back of cotton leaves. After solutions were dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed in an incubator with no sunlight, with a temperature of 27±1° C., with relative humidity of 60%±5%, and with photoperiod of 16L:8D. The identical spraying was carried out with dsEGFP as control. The results of adult mortality after 2 days of spraying were shown in FIG. 3 which shows that mortality of the adults sprayed with dsGawky bacterial solutions (47%) was significantly increased compared with the control.

Embodiment 10

The following was lethal effect of spraying the mixed solutions of nanomaterial TiC and transcribed dsGawky bacterial cells on adult Q-type silverleaf whiteflies.

Figure 4:
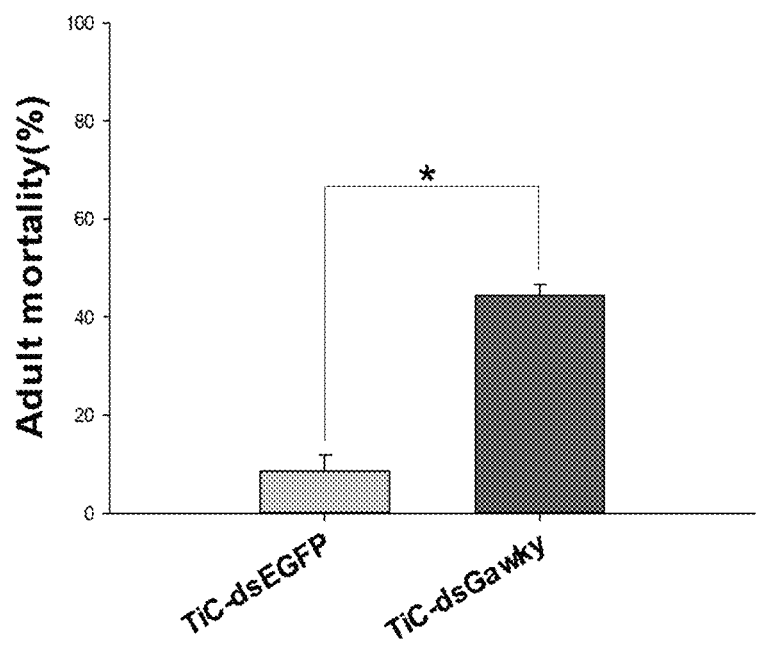
FIG. 4 shows the lethal effect of spraying the mixed solutions of nanomaterial TiC and transcribed dsGawky bacterial cells on adult Q-type silverleaf whiteflies. (TiC-dsEGFP is control group of spraying the mixed solutions of nanomaterial TiC and transcribed dsEGFP bacterial cells, TiC-dsGawky is treatment group of spraying mixed solutions of nanomaterial TiC and transcribed dsGawky bacterial cells and "*" indicates a significant difference between the two.)

The mixed solutions of nanomaterial TiC as well as transcribed dsGawky bacterial cells prepared in Embodiment 2 were sprayed on cotton plants, spraying 3 times on front and back of cotton leaves. After solutions were dried, 30 adult Q-type silverleaf whiteflies were released on a single cotton plant, and the treatment was repeated three times in total. The 3 treated cotton plants with 30 adult Q-type silverleaf whiteflies on each cotton plant were placed in an incubator with no sunlight, with a temperature of 27±1° C., with relative humidity of 60%±5%, and with photoperiod of 16L:8D. The identical spraying was carried out with dsEGFP as the control. The results of adult mortality after 2 days of spraying were shown in FIG. 4 which shows that the mortality of adults sprayed with dsGawky bacterial solutions (45%) was significantly increased compared with the control.

Embodiment 11

The following was the lethal effect of spraying mixed solutions of nanomaterial SiC and transcribed dsGawky bacterial cells on adult Q-type silverleaf whiteflies.

Figure 5:
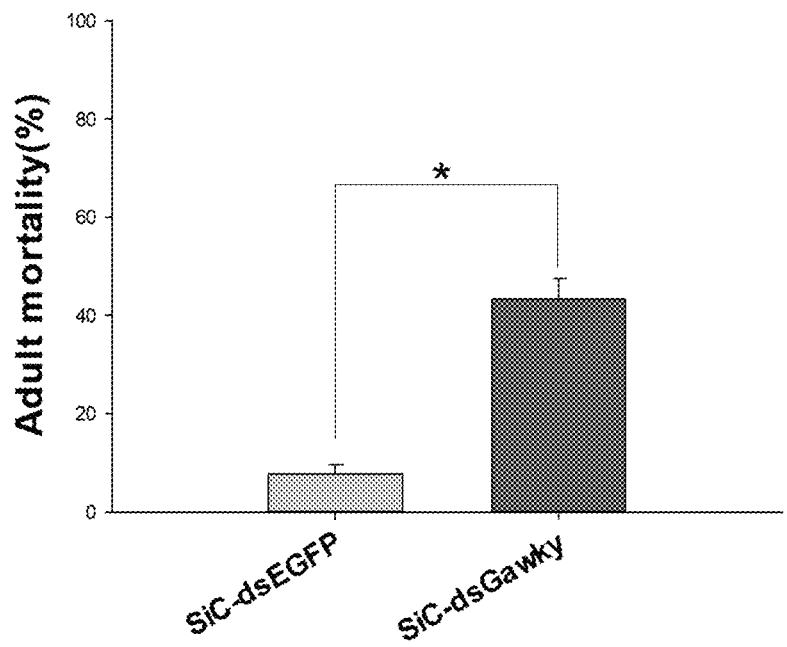
FIG. 5 shows the lethal effect of spraying the mixed solutions of nanomaterial SiC and transcribed dsGawky bacterial cells on adult Q-type silverleaf whiteflies. (SiC-dsEGFP is control group of spraying the mixed solutions of nanomaterial SiC and transcribed dsEGFP bacterial cells, SiC-dsGawky is treatment group of spraying mixed solutions of nanomaterial SiC and transcribed dsGawky bacterial cells and "*" indicates a significant difference between the two.)

The mixed solutions of nanomaterial SiC as well as transcribed dsGawky bacterial cells prepared in Embodiment 2 were sprayed on cotton plants, spraying 3 times on front and back of cotton leaves. After solutions were dried, 30 adult Q-type silverleaf whiteflies were released on a single cotton plant, and this treatment was repeated three times in total. The 3 treated cotton plants with 30 adult Q-type silverleaf whiteflies on each cotton plant were placed in an incubator with no sunlight, with a temperature of 27±1° C., with relative humidity of 60%±5%, and with photoperiod of 16L:8D. The identical spraying was carried out with dsEGFP as the control. The results of the adult mortality after 2 days of spraying were shown in FIG. 5 which shows that the adult mortality sprayed with dsGawky bacterial solutions (44%) was significantly increased compared with the control.

Embodiment 12

The following was the lethal effect of spraying bacterial solutions of transcribed dsGawky bacterial cells on adult Q-type silverleaf whiteflies under outdoor and UV light conditions.

Outdoor: The bacterial solutions of transcribed dsGawky bacterial cells were dissolved and diluted with ddH$_2$O to dilute it into bacterial solutions with wet bacterial concentration of 2 g/L, and then sprayed on cotton plants, spraying 3 times on front and back of the cotton leaves. After solutions were dried, 30 adult Q-type silverleaf whiteflies were released on a single cotton plant, and this treatment was repeated three times in total. The 3 treated cotton plants with 30 adult Q-type silverleaf whiteflies on each cotton plant were placed outdoors with the sunlight. The identical spraying was carried out with dsEGFP as the control, and mortality results of adults were counted 2 days after spraying.

UV Light: The dsRNA bacterial solutions of the silverleaf whiteflies were dissolved and diluted with ddH$_2$O to dilute it into the bacterial solutions with wet bacterial concentration of 2 g/L, and then sprayed on cotton plants, spraying 3 times on the front and back of cotton leaves. After 3 hours of irradiation with UV-Device and solutions were therefore dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed in the constant temperature box with a temperature of 27±1° C., with relative humidity of 60%±5%, and with photoperiod of 16L:8D. The identical spraying was carried out with dsEGFP as the control, and mortality results of adults were counted 2 days after spraying.

Figure 6:
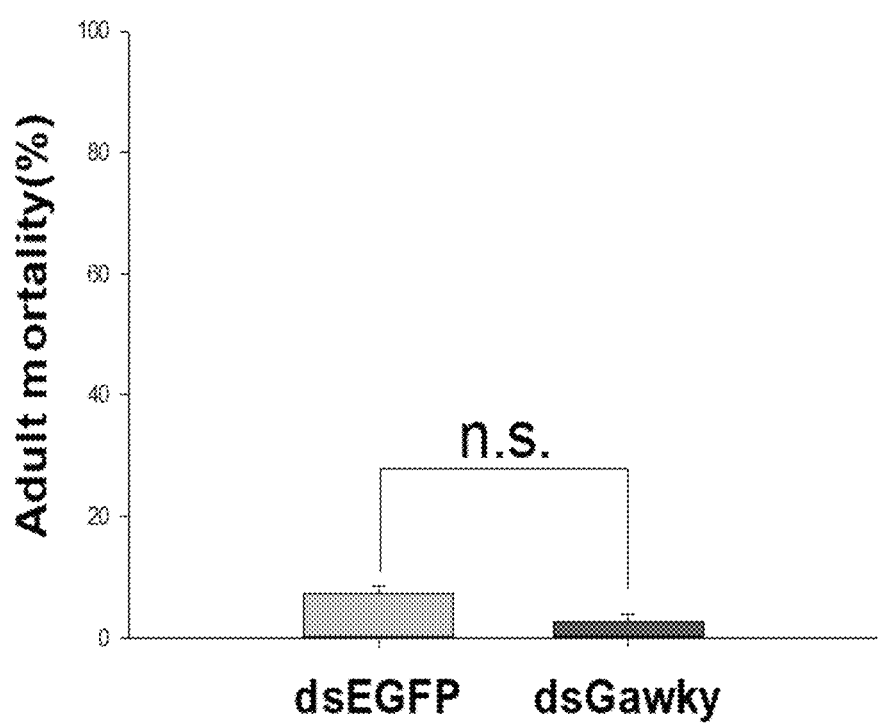
FIG. 6 shows lethal effect of spraying bacterial solutions transcribing dsGawky bacterial cells on the adult Q-type silverleaf whiteflies under outdoor conditions. (dsEGFP is control group of spraying bacterial cells transcribing dsEGFP, dsGawky is treatment group of spraying bacterial cells transcribing dsGawky and "n.s." indicates that there is no significant difference between the two.)

The lethal effect of spraying bacterial solutions of transcribed dsGawky bacterial cells on adult Q-type silverleaf whiteflies under the outdoor conditions was shown in FIG. 6 which shows that mortality of adults (3%) was not significant compared with the control by spraying bacterial solutions of transcribed dsRNA.

Figure 7:
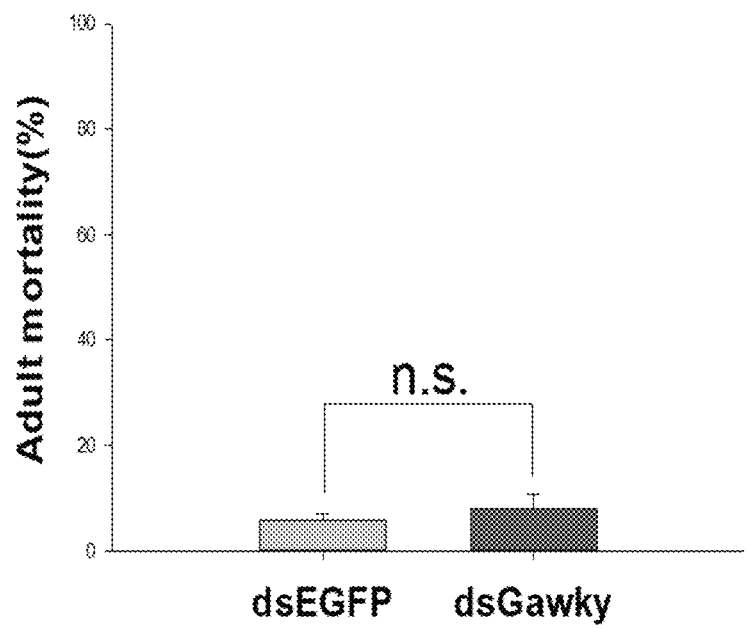
FIG. 7 shows lethal effect of spraying bacterial solutions transcribing dsGawky bacterial cells on the adult Q-type silverleaf whiteflies under UV light irradiation for three hours. (dsEGFP is control group of spraying the bacterial cells transcribing dsEGFP, dsGawky is treatment group of spraying the bacterial cells transcribing dsGawky and "n.s." indicates that there is no significant difference between the two.)

The lethal effect of spraying bacterial solutions of transcribed dsGawky bacterial cells on adult Q-type silverleaf whiteflies under UV light irradiation for 3 hours was shown in FIG. 7 which shows that the mortality of adults (8%) was not significant compared with the control by spraying bacterial solutions of transcribed dsRNA.

Embodiment 13

The following was lethal effect of spraying mixed solutions of nanomaterial MON and transcribed dsGawky bacterial cells on adult Q-type silverleaf whiteflies under outdoor and UV light conditions.

Outdoor: The mixed solutions of nanomaterial MON and transcribed dsGawky bacterial cells prepared in Embodiment 3 were sprayed on cotton plants, spraying 3 times on front and back of cotton leaves. After solutions were dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed outdoors with sunlight. The mixed solutions of nanomaterial MON as well as dsEGFP were used as negative control, and the aqueous solutions of nanomaterial MON were used as blank control for the same spraying. The adult mortality results were counted 2 days after spraying.

UV Light: The mixed solutions of nanomaterial MON as well as the transcribed dsGawky bacterial cells prepared in Embodiment 3 were sprayed on cotton plants, spraying 3 times on front and back of cotton leaves. After 3 hours of irradiation with the UV-Device and the solutions were therefore dried, 30 adult Q-type silverleaf whiteflies were released on a single cotton plant, and this treatment was repeated three times in total. The 3 treated cotton plants with 30 adult Q-type silverleaf whiteflies on each cotton plant were placed in constant temperature box with temperature of 27±1° C., with the relative humidity of 60%±5%, and with the photoperiod of 16L:8D. The mixed solutions of nanomaterial MON and dsEGFP were used as negative control, and aqueous solutions of the nanomaterial MON were used as blank control for the identical spraying. The adult mortality results were counted 2 days after spraying.

Figure 8:
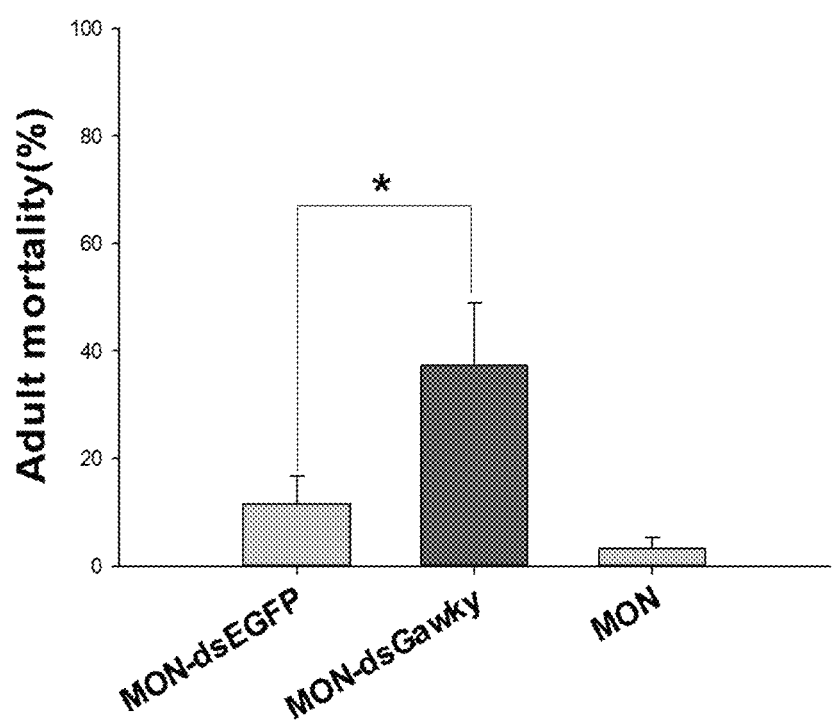
FIG. 8 shows the lethal effect of spraying the mixed solutions of nanomaterial MON and transcribed dsGawky bacterial cells on adult Q-type silverleaf whiteflies under outdoor conditions. (MON-dsEGFP is the control group of spraying the mixed solutions of nanomaterial MON and transcribed dsEGFP bacterial cells, MON-dsGawky is the treatment group of spraying the mixed solutions of nanomaterial MON and transcribed dsGawky bacterial cells, MON is the blank control group of spraying the aqueous solutions of the nanomaterial MON and "*" indicates a significant difference between the two.)

The lethal effect of spraying the mixed solutions of nanomaterial MON and transcribed dsGawky bacterial cells on adult Q-type silverleaf whiteflies under outdoor conditions was shown in FIG. 8 which shows that mortality of adults (37%) was significantly increased compared with the control by spraying the mixed solutions.

Figure 9:
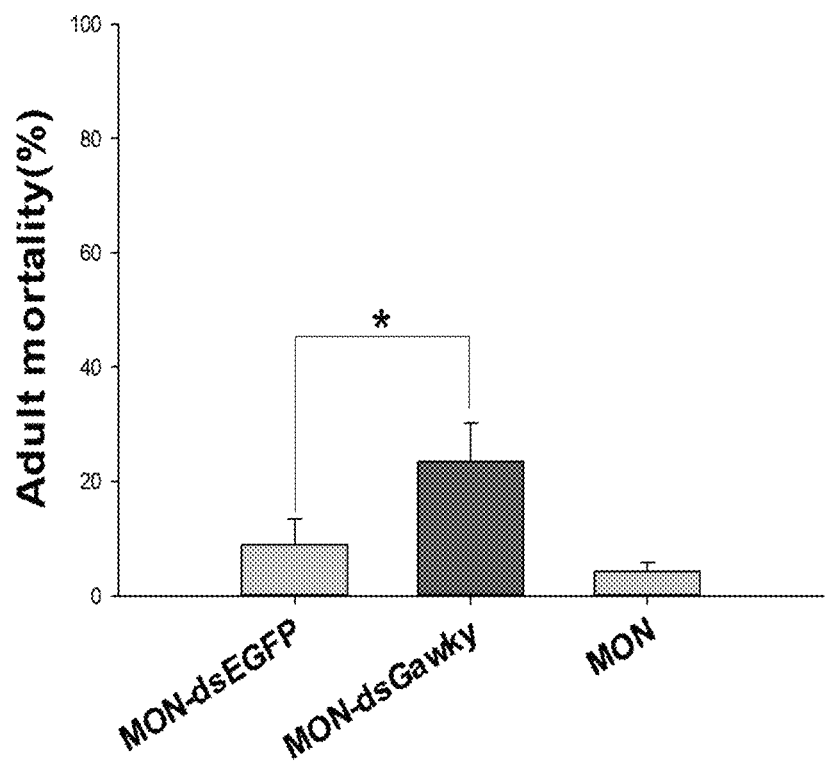
FIG. 9 shows the lethal effect of spraying the mixed solutions of nanomaterial MON and transcribed dsGawky bacterial cells on adult Q-type silverleaf whiteflies under UV light irradiation for 3 hours. (MON-dsEGFP is the control group of spraying the mixed solutions of nanomaterial MON and transcribed dsEGFP bacterial cells, MON-dsGawky is the treatment group of spraying the mixed solutions of nanomaterial MON and transcribed dsGawky bacterial cells, MON is the blank control group of spraying the aqueous solutions of the nanomaterial MON and "*" indicates a significant difference between the two.)

The lethal effect of spraying the mixed solutions of nanomaterial MON and transcribed dsGawky bacterial cells on adult Q-type silverleaf whiteflies under UV light irradiation for three hours was shown in FIG. 9 which shows that mortality of adults (24%) was significantly increased compared with the control by spraying the mixed solutions.

Embodiment 14

The following was lethal effect of spraying mixed solutions of nanomaterial $Fe_3O_4$ and transcribed dsGawky bacterial cells on adult Q-type silverleaf whiteflies under outdoor and UV light conditions.

Outdoor: The mixed solutions of nanomaterial $Fe_3O_4$ and transcribed dsGawky bacterial cells prepared in Embodiment 4 were sprayed on cotton plants, spraying 3 times on front and back of cotton leaves. After solutions were dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed outdoors with sunlight. The mixed solutions of nanomaterial $Fe_3O_4$ and dsEGFP were used as negative control. The adult mortality results were counted 2 days after spraying.

UV Light: The mixed solutions of the nanomaterial $Fe_3O_4$ and the transcribed dsGawky bacterial cells prepared in Embodiment 4 were sprayed on cotton plants, spraying 3 times on front and back of cotton leaves. After three hours of irradiation with the UV-Device and solutions were therefore dried, 30 adult Q-type silverleaf whiteflies were released on a single cotton plant, and this treatment was repeated 3 times in total. The three treated cotton plants with 30 adult Q-type silverleaf whiteflies on each cotton plant were placed in constant temperature box with temperature of 27±1° C., with the relative humidity of 60%±5%, and with the photoperiod of 16L:8D. The mixed solutions of nanomaterial $Fe_3O_4$ and dsEGFP were used as negative control. The adult mortality results were counted 2 days after spraying.

Figure 10:
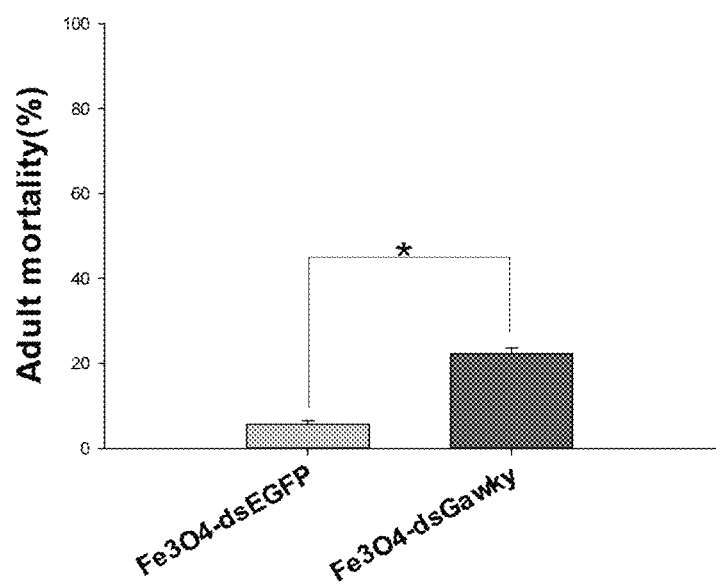
FIG. 10 shows the lethal effect of spraying the mixed solutions of nanomaterial $Fe_3O_4$ and transcribed dsGawky bacterial cells on adult Q-type silverleaf whiteflies under outdoor conditions. ($Fe_3O_4$-dsEGFP is the control group of spraying the mixed solutions of nanomaterial $Fe_3O_4$ and transcribed dsEGFP bacterial cells, $Fe_3O_4$-dsGawky is the treatment group of spraying the mixed solutions of the nanomaterial $Fe_3O_4$ and the transcribed dsGawky bacterial cells and "*" indicates a significant difference between the two.)

The lethal effect of spraying the mixed solutions of nanomaterial $Fe_3O_4$ and transcribed dsGawky bacterial cells on adult Q-type silverleaf whiteflies under outdoor conditions was shown in FIG. 10 which shows that the mortality of adults (22%) was significantly increased compared with the control by spraying the mixed solutions.

Figure 11:
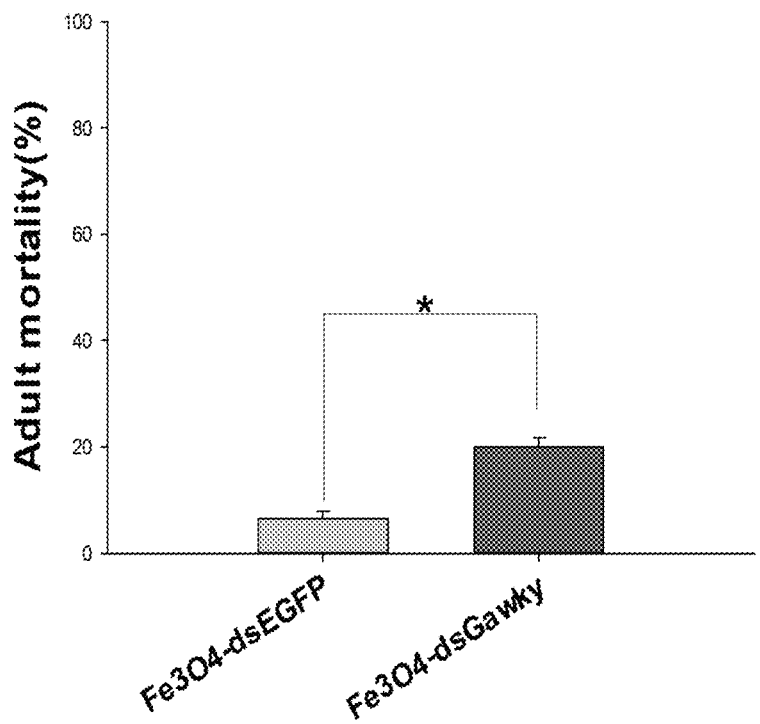
FIG. 11 shows the lethal effect of spraying the mixed solutions of nanomaterial $Fe_3O_4$ and transcribed dsGawky bacterial cells on adult Q-type silverleaf whiteflies under UV light irradiation for 3 hours. ($Fe_3O_4$-dsEGFP is the control group of spraying the mixed solutions of nanomaterial $Fe_3O_4$ and transcribed dsEGFP bacterial cells, $Fe_3O_4$-dsGawky is the treatment group of spraying the mixed solutions of the nanomaterial $Fe_3O_4$ and the transcribed dsGawky bacterial cells and "*" indicates a significant difference between the two.)

The lethal effect of spraying the mixed solutions of nanomaterial $Fe_3O_4$ and transcribed dsGawky bacterial cells on adult Q-type silverleaf whiteflies under UV light irradiation for three hours was shown in FIG. 11 which shows that the mortality of the adults (19%) was significantly increased compared with the control by spraying the mixed solutions.

Embodiment 15

The following was the lethal effect of spraying mixed solutions of nanomaterial TiC and transcribed dsGawky bacterial cells on adult Q-type silverleaf whiteflies under outdoor and UV light conditions.

Outdoor: The mixed solutions of the nanomaterial TiC as well as the transcribed dsGawky bacterial cells prepared in Embodiment 5 were sprayed on cotton plants, spraying 3 times on front and back of cotton leaves. After solutions were dried, 30 adult Q-type silverleaf whiteflies were released on a single cotton plant, and this treatment was repeated 3 times in total. The three treated cotton plants with 30 adult Q-type silverleaf whiteflies on each cotton plant were placed outdoors with sunlight. The mixed solutions of nanomaterial TiC and dsEGFP were used as negative control. The adult mortality results were counted 2 days after spraying.

UV Light: The mixed solutions of the nanomaterial TiC as well as transcribed dsGawky bacterial cells prepared in Embodiment 5 were sprayed on cotton plants, spraying 3 times on front and back of cotton leaves. After 3 hours of irradiation with the UV-Device and solutions were therefore dried, 30 adult Q-type silverleaf whiteflies were released on a single cotton plant, and this treatment was repeated 3 times in total. The three treated cotton plants with 30 adult Q-type silverleaf whiteflies on each cotton plant were placed in constant temperature box with temperature of 27±1° C., with the relative humidity of 60%±5%, and with photoperiod of 16L:8D. The mixed solutions of nanomaterial TiC and dsEGFP were used as the negative control. The adult mortality results were counted 2 days after spraying.

Figure 12:
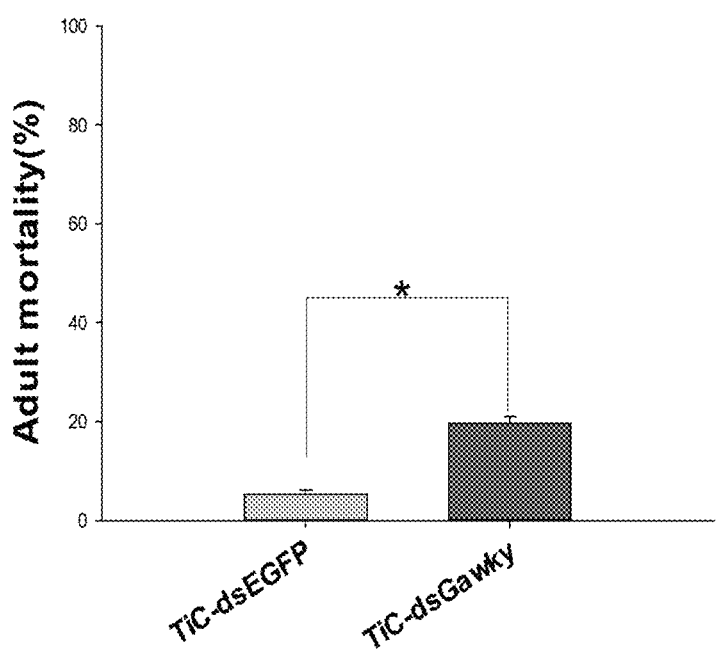
FIG. 12 shows the lethal effect of spraying the mixed solutions of nanomaterial TiC and transcribed dsGawky bacterial cells on adult Q-type silverleaf whiteflies under outdoor conditions. (TiC-dsEGFP is control group of spraying the mixed solutions of nanomaterial TiC and transcribed dsEGFP bacterial cells, TiC-dsGawky is the treatment group of spraying the mixed solutions of the nanomaterial TiC and the transcribed dsGawky bacterial cells and "*" indicates a significant difference between the two.)

The lethal effect of spraying mixed solutions of the nanomaterial TiC and the transcribed dsGawky bacterial cells on adult Q-type silverleaf whiteflies under outdoor conditions was shown in FIG. 12 which shows that mortality of adults (19%) was significantly increased compared with the control by spraying the mixed solutions.

Figure 13:
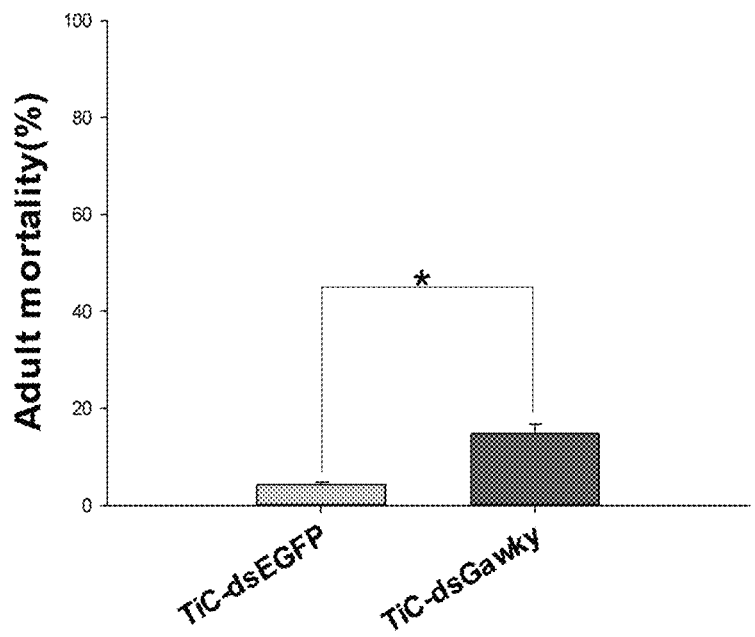
FIG. 13 shows the lethal effect of spraying the mixed solutions of nanomaterial TiC and transcribed dsGawky bacterial cells on adult Q-type silverleaf whiteflies under UV light irradiation for 3 hours. (TiC-dsEGFP is control group of spraying the mixed solutions of nanomaterial TiC and transcribed dsEGFP bacterial cells, TiC-dsGawky is the treatment group of spraying the mixed solutions of the nanomaterial TiC and the transcribed dsGawky bacterial cells and "*" indicates a significant difference between the two.)

The lethal effect of spraying mixed solutions of the nanomaterial TiC and the transcribed dsGawky bacterial cells on adult Q-type silverleaf whiteflies under UV light irradiation for three hours was shown in FIG. 13 which shows that the mortality of the adults (15%) was significantly increased compared with the control by spraying the mixed solutions.

Embodiment 16

The following was the lethal effect of spraying mixed solutions of nanomaterial SiC and transcribed dsGawky bacterial cells on adult Q-type silverleaf whiteflies under outdoor and UV light conditions.

Outdoor: The mixed solutions of the nanomaterial SiC as well as the transcribed dsGawky bacterial cells prepared in Embodiment 6 were sprayed on cotton plants, spraying 3 times on front and back of cotton leaves. After solutions were dried, 30 adult Q-type silverleaf whiteflies were released on a single cotton plant, and this treatment was repeated 3 times in total. The three treated cotton plants with 30 adult Q-type silverleaf whiteflies on each cotton plant were placed outdoors with sunlight. The mixed solutions of nanomaterial SiC and dsEGFP were used as negative control. The adult mortality results were counted 2 days after spraying.

UV Light: The mixed solutions of the nanomaterial SiC as well as transcribed dsGawky bacterial cells prepared in Embodiment 6 were sprayed on cotton plants, spraying 3 times on front and back of cotton leaves. After 3 hours of irradiation with UV-Device and the solutions were therefore dried, 30 adult Q-type silverleaf whiteflies were released on a single cotton plant, and this treatment was repeated 3 times in total. The three treated cotton plants with 30 adult Q-type silverleaf whiteflies on each cotton plant were placed in constant temperature box with temperature of 27±1° C., with the relative humidity of 60%±5%, and with photoperiod of 16L:8D. The mixed solutions of nanomaterial SiC and dsEGFP were used as the negative control. The adult mortality results were counted 2 days after spraying.

Figure 14:
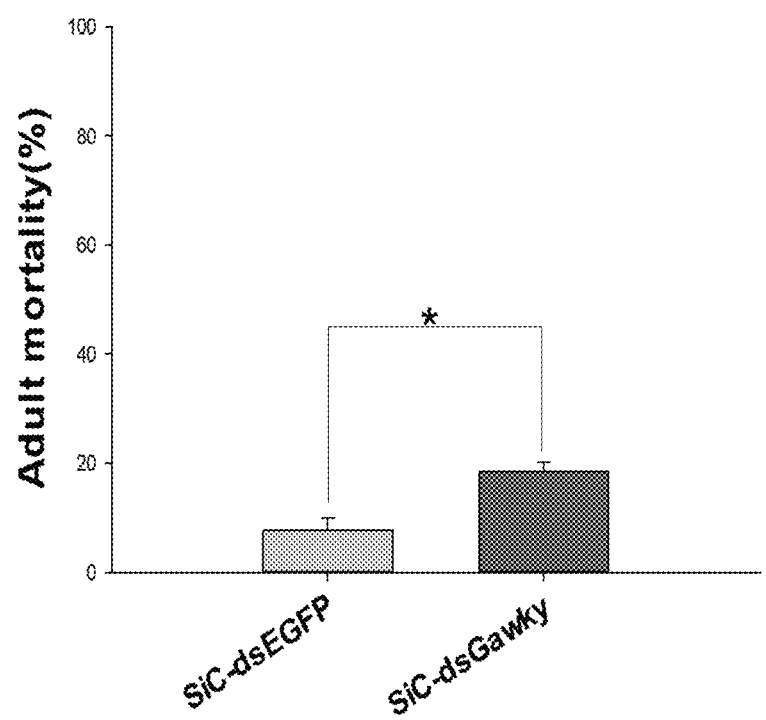
FIG. 14 shows the lethal effect of spraying the mixed solutions of nanomaterial SiC and transcribed dsGawky bacterial cells on adult Q-type silverleaf whiteflies under outdoor conditions. (SiC-dsEGFP is control group of spraying the mixed solutions of nanomaterial SiC and transcribed dsEGFP bacterial cells, SiC-dsGawky is the treatment group of spraying the mixed solutions of the nanomaterial SiC and the transcribed dsGawky bacterial cells and "*" indicates a significant difference between the two.)

The lethal effect of spraying mixed solutions of the nanomaterial SiC and the transcribed dsGawky bacterial cells on adult Q-type silverleaf whiteflies under outdoor conditions was shown in FIG. 14 which shows that mortality of adults (18%) was significantly increased compared with the control by spraying the mixed solutions.

Figure 15:
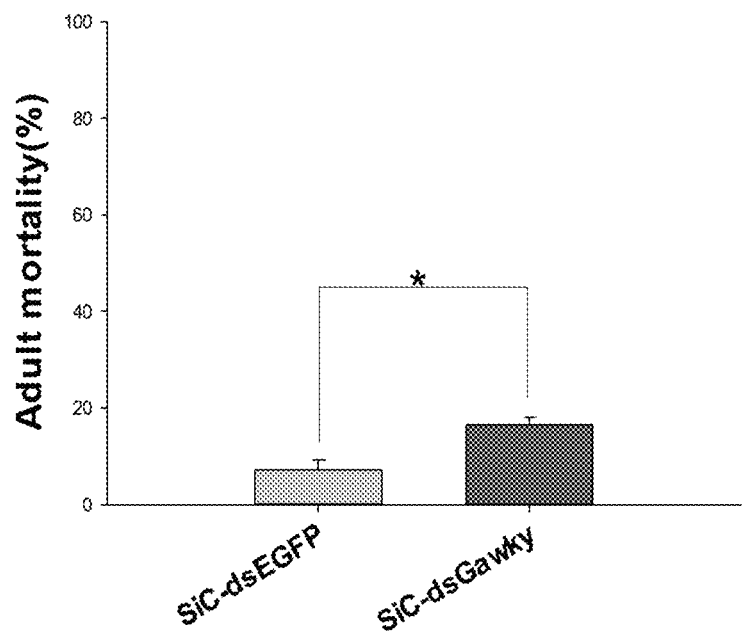
FIG. 15 shows the lethal effect of spraying the mixed solutions of nanomaterial SiC and transcribed dsGawky bacterial cells on adult Q-type silverleaf whiteflies under UV light irradiation for 3 hours. (SiC-dsEGFP is control group of spraying the mixed solutions of nanomaterial SiC and transcribed dsEGFP bacterial cells, SiC-dsGawky is the treatment group of spraying the mixed solutions of the nanomaterial SiC and the transcribed dsGawky bacterial cells and "*" indicates a significant difference between the two.)

The lethal effect of spraying mixed solutions of the nanomaterial SiC and the transcribed dsGawky bacterial cells on adult Q-type silverleaf whiteflies under UV light irradiation for 3 hours was shown in FIG. 15 which shows that the mortality of adults (17%) was significantly increased compared with the control by spraying the mixed solutions.

Comparative Embodiment

The following was the lethal effect of spraying mixed solutions on adult Q-type silverleaf whiteflies under UV light conditions.

The nanomaterials $MnO_2$, $TiO_2$, $CeO_2$, CuS, $CB_4$, ZrC, $Al_2O_3$, $N_4Si_3$, $Co_3O_4$ as well as AlN were respectively prepared into the mixed solutions with transcribed dsGawky bacterial cells, preparation method of which was as follows:

1) Preparing nanomaterial into aqueous solutions with identical concentration (2 g/L) as the solutions of transcribed dsGawky bacterial cells.

2) Mixing the aqueous solutions of nanomaterial with solutions of transcribed dsGawky bacterial cells in the volume ratio of 6:1, and after 30 min of shaking and mixing, mixed solutions of nanomaterial and transcribed dsGawky bacterial cells for the RNAi interference of the silverleaf whiteflies can be obtained.

Solutions of transcribed dsGawky bacterial cells can be prepared by method described in the Chinese patent application "GAWKY GENE OF THE SILVERLEAF WHITEFLIES AND APPLICATION THEREOF IN BIOLOGICAL CONTROL OF SILVERLEAF WHITEFLIES" with Publication Number CN116732042A. When in use, $ddH_2O$ was used for dissolution as well as dilution to dilute it into bacterial solutions with wet bacterial concentration of 2 g/L.

The mixed solutions of nanomaterial $MnO_2$, $TiO_2$, $CeO_2$, CuS, $CB_4$, ZrC, $Al_2O_3$, $N_4Si_3$, $Co_3O_4$ or AlN and transcribed dsGawky bacterial cells prepared in above were sprayed on cotton plants, spraying 3 times on front and back of the cotton leaves. After 3 hours of the irradiation with UV-Device and solutions were therefore dried, 30 adult Q-type silverleaf whiteflies were released on a single cotton plant, and this treatment was repeated 3 times in total. The 3 treated cotton plants with 30 adult Q-type silverleaf whiteflies on each cotton plant were placed in constant temperature box with a temperature of 27±1° C., with the relative humidity of 60%±5%, and with photoperiod of 16L:8D. The mixed solutions of nanomaterial $MnO_2$, $TiO_2$, $CeO_2$, CuS, $CB_4$, ZrC, $Al_2O_3$, $N_4Si_3$, $Co_3O_4$ or AlN and dsEGFP were used as negative control. The mortality results of the adults were counted 2 days after spraying.

Figure 16:
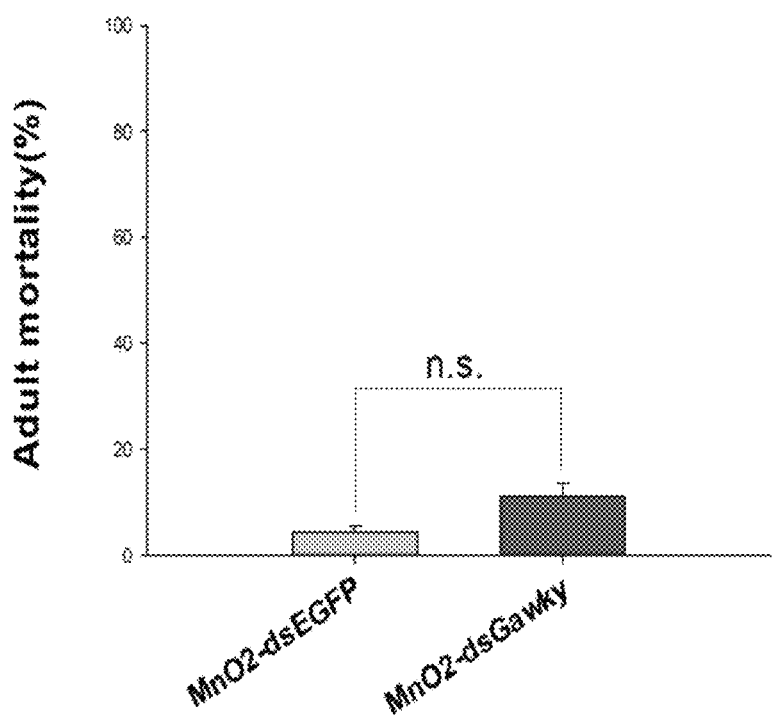
FIG. 16 shows lethal effect of spraying the mixed solutions of nanomaterial $MnO_2$ and transcribed dsGawky bacterial cells on adult Q-type silverleaf whiteflies under UV light irradiation for 3 hours. ($MnO_2$-dsEGFP is control group of spraying mixed solutions of nanomaterial $MnO_2$ and transcribed dsEGFP bacterial cells, $MnO_2$-dsGawky is treatment group of spraying the mixed solutions of nanomaterial $MnO_2$ and transcribed dsGawky bacterial cells and "n.s." indicates that there is no significant difference between the two.)

The results of adult mortality of spraying mixed solutions of nanomaterial $MnO_2$ as well as transcribed dsGawky bacterial cells on adult Q-type silverleaf whiteflies after 3 hours of UV light irradiation were shown in FIG. 16 which shows that the adult mortality (11.27%) was not significant compared with the control by spraying the mixed solutions.

Figure 17:
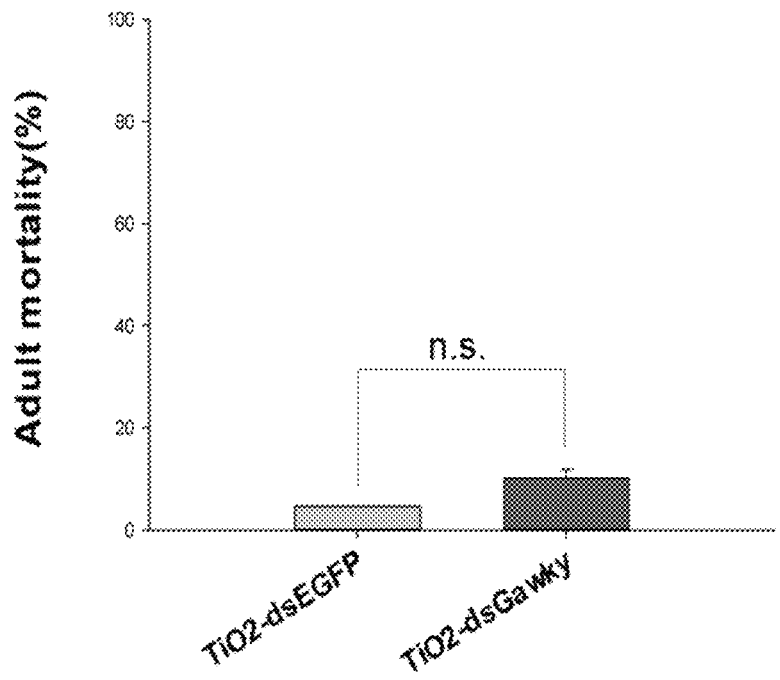
FIG. 17 shows the lethal effect of spraying the mixed solutions of nanomaterial $TiO_2$ and transcribed dsGawky bacterial cells on adult Q-type silverleaf whiteflies under UV light irradiation for 3 hours. ($TiO_2$-dsEGFP is control group of spraying mixed solutions of nanomaterial $TiO_2$ and transcribed dsEGFP bacterial cells, $TiO_2$-dsGawky is treatment group of spraying mixed solutions of nanomaterial $TiO_2$ and the transcribed dsGawky bacterial cells and "n.s." indicates that there is no significant difference between the two.)

The results of adult mortality of spraying mixed solutions of nanomaterial $TiO_2$ as well as transcribed dsGawky bacterial cells on adult Q-type silverleaf whiteflies after 3 hours of UV light irradiation were shown in FIG. 17 which shows that the adult mortality (10.16%) was not significant compared with the control by spraying the mixed solutions.

Figure 18:
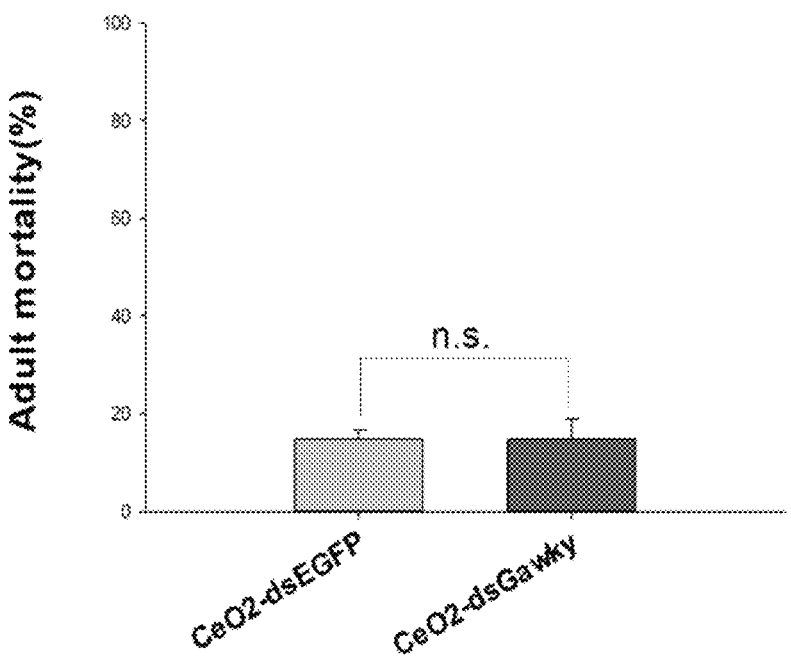
FIG. 18 shows the lethal effect of spraying the mixed solutions of nanomaterial $CeO_2$ and transcribed dsGawky bacterial cells on adult Q-type silverleaf whiteflies under UV light irradiation for 3 hours. ($CeO_2$-dsEGFP is control group of spraying the mixed solutions of nanomaterial $CeO_2$ and transcribed dsEGFP bacterial cells, $CeO_2$-dsGawky is treatment group of spraying the mixed solutions of the nanomaterial $CeO_2$ and the transcribed dsGawky bacterial cells and "n.s." indicates that there is no significant difference between the two.)

The results of adult mortality of spraying mixed solutions of nanomaterial $CeO_2$ as well as transcribed dsGawky bacterial cells on adult Q-type silverleaf whiteflies after 3 hours of UV light irradiation were shown in FIG. 18 which shows that the adult mortality (14.79%) was not significant compared with the control by spraying the mixed solutions.

Figure 19:
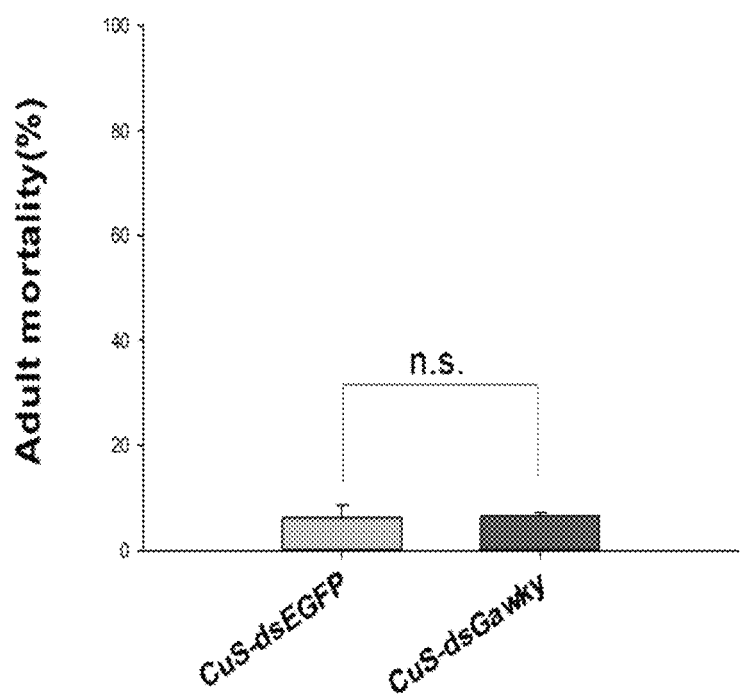
FIG. 19 shows the lethal effect of spraying the mixed solutions of nanomaterial CuS and transcribed dsGawky bacterial cells on adult Q-type silverleaf whiteflies under UV light irradiation for three hours. (CuS-dsEGFP is control group of spraying mixed solutions of nanomaterial CuS and transcribed dsEGFP bacterial cells, CuS-dsGawky is treatment group of spraying the mixed solutions of the nanomaterial CuS and the transcribed dsGawky bacterial cells and "n.s." indicates that there is no significant difference between the two.)

The results of adult mortality of spraying mixed solutions of nanomaterial CuS as well as transcribed dsGawky bacterial cells on adult Q-type silverleaf whiteflies after 3 hours of UV light irradiation were shown in FIG. 19 which shows that adult mortality (6.61%) was not significant compared with the control by spraying the mixed solutions.

Figure 20:
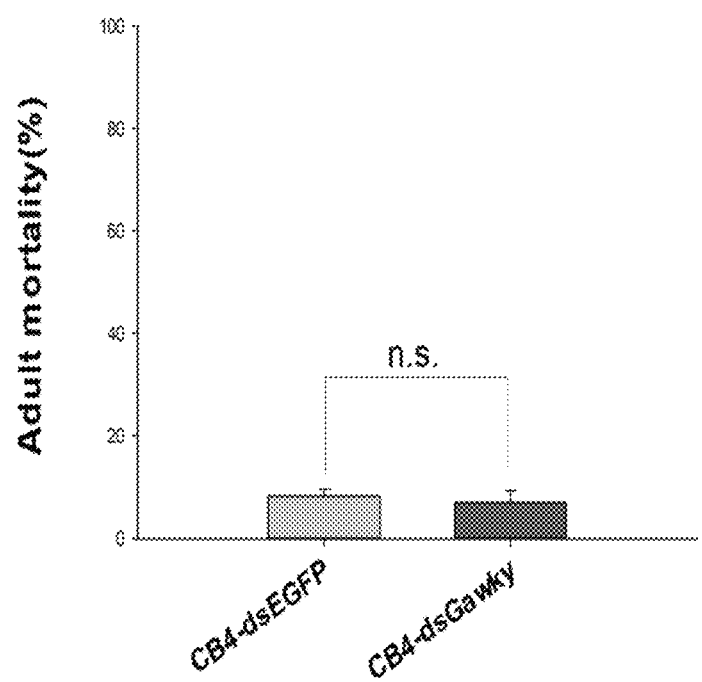
FIG. 20 shows the lethal effect of spraying the mixed solutions of nanomaterial $CB_4$ and transcribed dsGawky bacterial cells on adult Q-type silverleaf whiteflies under UV light irradiation for three hours. ($CB_4$-dsEGFP is control group of spraying mixed solutions of nanomaterial $CB_4$ and transcribed dsEGFP bacterial cells, $CB_4$-dsGawky is treatment group of spraying the mixed solutions of the nanomaterial $CB_4$ and the transcribed dsGawky bacterial cells and "n.s." indicates that there is no significant difference between the two.)

The results of adult mortality of spraying mixed solutions of nanomaterial $CB_4$ as well as transcribed dsGawky bacterial cells on adult Q-type silverleaf whiteflies after 3 hours of UV light irradiation were shown in FIG. 20 which shows that adult mortality (7.07%) was not significant compared with the control by spraying the mixed solutions.

Figure 21:
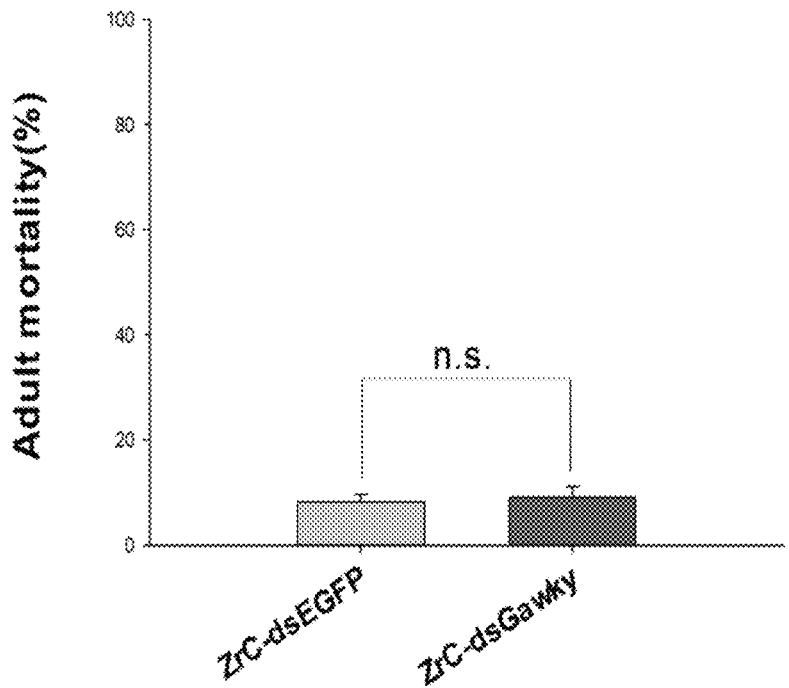
FIG. 21 shows the lethal effect of spraying the mixed solutions of nanomaterial ZrC and transcribed dsGawky bacterial cells on adult Q-type silverleaf whiteflies under UV light irradiation for three hours. (ZrC-dsEGFP is control group of spraying mixed solutions of nanomaterial ZrC and transcribed dsEGFP bacterial cells, ZrC-dsGawky is treatment group of spraying the mixed solutions of the nanomaterial ZrC and the transcribed dsGawky bacterial cells and "n.s." indicates that there is no significant difference between the two.)

The results of adult mortality of spraying mixed solutions of nanomaterial ZrC as well as transcribed dsGawky bacterial cells on adult Q-type silverleaf whiteflies after 3 hours of UV light irradiation were shown in FIG. 21 which shows that adult mortality (9.13%) was not significant compared with the control by spraying the mixed solutions.

Figure 22:
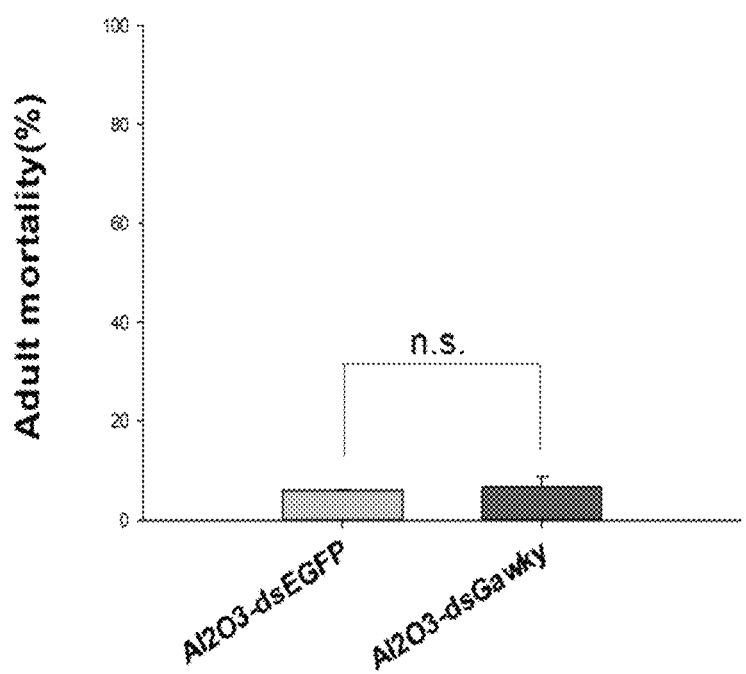
FIG. 22 shows the lethal effect of spraying the mixed solutions of nanomaterial $Al_2O_3$ and transcribed dsGawky bacterial cells on the adult Q-type silverleaf whiteflies under UV light irradiation for three hours. ($Al_2O_3$-dsEGFP is control group of spraying the mixed solutions of nanomaterial $Al_2O_3$ and transcribed dsEGFP bacterial cells, $Al_2O_3$-dsGawky is treatment group of spraying the mixed solutions of nanomaterial $Al_2O_3$ and transcribed dsGawky bacterial cells and "n.s." indicates that there is no significant difference between the two.)

The results of adult mortality of spraying mixed solutions of nanomaterial $Al_2O_3$ as well as transcribed dsGawky bacterial cells on adult Q-type silverleaf whiteflies after 3 hours of UV light irradiation were shown in FIG. 22 which shows that the adult mortality (6.64%) was not significant compared with the control by spraying the mixed solutions.

Figure 23:
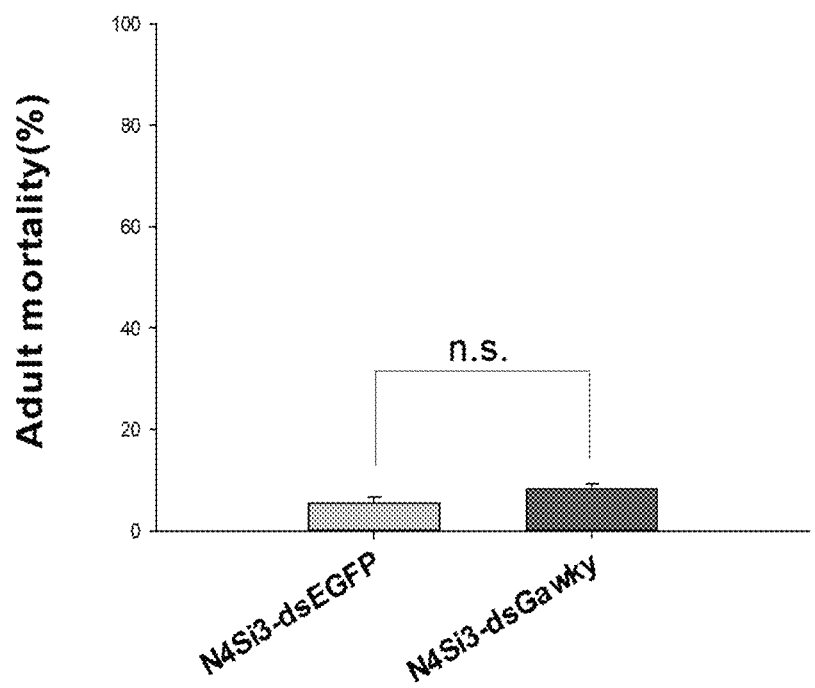
FIG. 23 shows the lethal effect of spraying the mixed solutions of nanomaterial $N_4Si_3$ and transcribed dsGawky bacterial cells on adult Q-type silverleaf whiteflies under UV light irradiation for three hours. ($N_4Si_3$-dsEGFP is control group of spraying mixed solutions of nanomaterial $N_4Si_3$ and transcribed dsEGFP bacterial cells, $N_4Si_3$-dsGawky is treatment group of spraying the mixed solutions of the nanomaterial $N_4Si_3$ and the transcribed dsGawky bacterial cells and "n.s." indicates that there is no significant difference between the two.)

The results of adult mortality of spraying mixed solutions of nanomaterial $N_4Si_3$ as well as transcribed dsGawky bacterial cells on adult Q-type silverleaf whiteflies after 3 hours of UV light irradiation were shown in FIG. 23 which shows that the adult mortality (8.21%) was not significant compared with the control by spraying the mixed solutions.

Figure 24:
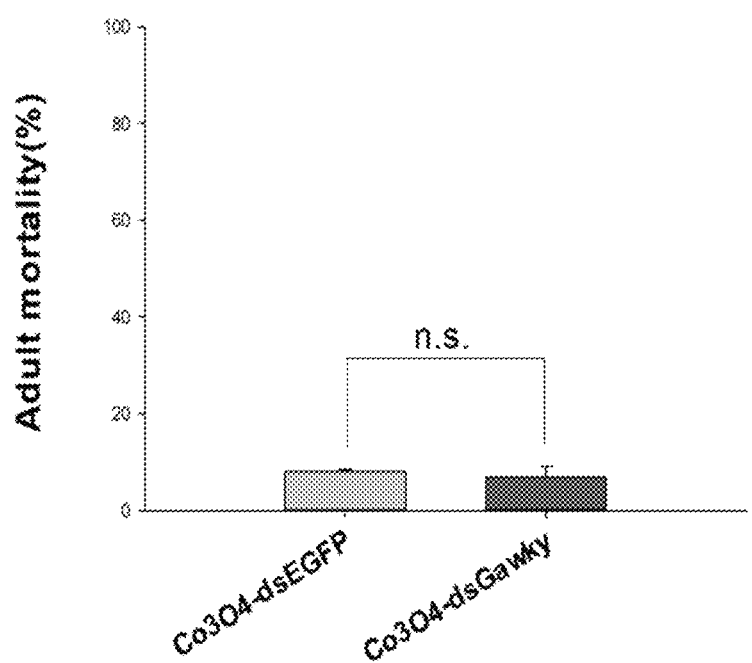
FIG. 24 shows lethal effect of spraying the mixed solutions of nanomaterial $Co_3O_4$ and transcribed dsGawky bacterial cells on adult Q-type silverleaf whiteflies under UV light irradiation for 3 hours. ($Co_3O_4$-dsEGFP is control group of spraying mixed solutions of nanomaterial $Co_3O_4$ and transcribed dsEGFP bacterial cells, $Co_3O_4$-dsGawky is treatment group of spraying the mixed solutions of nanomaterial $Co_3O_4$ and transcribed dsGawky bacterial cells and "n.s." indicates that there is no significant difference between the two.)

The results of adult mortality of spraying mixed solutions of nanomaterial $Co_3O_4$ as well as transcribed dsGawky bacterial cells on adult Q-type silverleaf whiteflies after 3 hours of UV light irradiation were shown in FIG. 24 which shows that the adult mortality (6.93%) was not significant compared with the control by spraying the mixed solutions.

Figure 25:
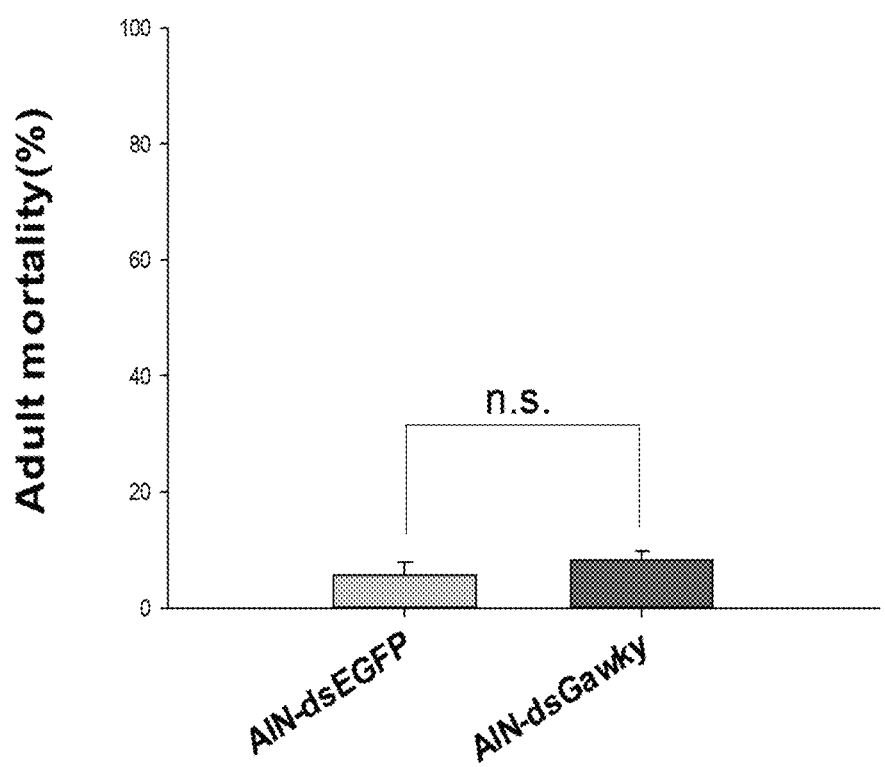
FIG. 25 shows lethal effect of spraying the mixed solutions of nanomaterial AlN and transcribed dsGawky bacterial cells on adult Q-type silverleaf whiteflies under UV light irradiation for 3 hours. (AlN-dsEGFP is control group of spraying mixed solutions of nanomaterial AlN and transcribed dsEGFP bacterial cells, AlN-dsGawky is treatment group of spraying mixed solutions of the nanomaterial AlN and the transcribed dsGawky bacterial cells and "n.s." indicates that there is no significant difference between the two.)

The results of adult mortality of spraying mixed solutions of nanomaterial AlN as well as transcribed dsGawky bacterial cells on adult Q-type silverleaf whiteflies after 3 hours of UV light irradiation were shown in FIG. 25 which shows that the adult mortality (8.33%) was not significant compared with the control by spraying the mixed solutions.

The above is only the preferred embodiments of the present invention and does not limit the present invention in other forms. Any technician familiar with the profession may use the above disclosed technical content to change or modify it into an equivalent embodiment with equivalent changes. However, any simple modification, equivalent change as well as modification made to above embodiments according to the technical essence of the present invention without departing from technical solution of the present invention still belongs to the protection scope of the technical solution of the present invention.

What is claimed is:

1. A method for preventing a dsRNA bacterial solution from being degraded by ultraviolet (UV) light comprising mixing the dsRNA bacterial solutions with the nanomaterial solutions to prepare mixed solutions of the nanomaterial and the dsRNA bacterial solutions, wherein the nanomaterial is mesoporous organosilica (MON), wherein the dsRNA bacterial solution is prepared using *E. coli* HT115(DE3) strain.

2. A biological agent for controlling silverleaf whiteflies, comprising nanomaterial and dsRNA bacterial solutions interfering with the Gawky gene of silverleaf whiteflies, wherein nanomaterial is mesoporous organosilica (MON).

3. The biological agent for controlling silverleaf whiteflies according to claim 2, wherein dsRNA bacterial solutions interfering with the Gawky gene of silverleaf whiteflies are bacterial solutions that transcribe the dsRNA of Gawky gene of silverleaf whiteflies, wherein the dsRNA bacterial solution is prepared using *E. coli* HT115(DE3) strain.

4. The biological agent for controlling silverleaf whiteflies according to claim 3, wherein bacterial solutions transcribing dsRNA of Gawky gene of silverleaf whiteflies are prepared by the following method:
using primers to amplify dsRNA sequence of Gawky gene, connecting it to expression vector, constructing recombinant vector, and transforming expression strain; inducing expression strain to transcribe the dsRNA sequence of Gawky gene, discarding the supernatant solutions in bacterial solutions, and dissolving as well as diluting it with ddH$_2$O to obtain the results.

5. The biological agent for controlling silverleaf whiteflies according to claim 4, wherein method for inducing expression strain to transcribe dsRNA sequence of Gawky gene is as follows:
inoculating recombinant bacteria transformed with the recombinant vector expressing dsRNA of Gawky gene of silverleaf whiteflies into LB medium containing Amp, culturing at 37° C. with shaking at 20 r/min, and when the OD$_{600}$ value of the bacterial solutions reaches 0.5, adding isopropyl-β-D-Thiogalactoside (IPTG) solutions with final concentration of 0.5M to induce for 4 hours to obtain the results.

6. The preparation method of above biological agent for controlling silverleaf whiteflies according to claim 3, comprising the following steps:
preparing nanomaterial into the aqueous solutions with identical concentration as the bacterial solutions transcribing dsRNA of Gawky gene of silverleaf whiteflies, and
mixing aqueous solutions of nanomaterial with the bacterial solutions transcribing dsRNA of Gawky gene of silverleaf whiteflies at a volume ratio of 6:1, and shaking as well as mixing for 30 minutes to obtain mixed solutions of nanomaterial and bacterial solutions transcribing the dsRNA of Gawky gene of silverleaf whiteflies used for RNAi interference of the silverleaf whiteflies.

* * * * *

SEQUENCE LISTING

```
Sequence total quantity: 3
SEQ ID NO: 1               moltype = DNA   length = 4554
FEATURE                    Location/Qualifiers
source                     1..4554
                           mol_type = other DNA
                           organism = Bemisia tabaci
SEQUENCE: 1
atgaactctt ctctctcctc cctctacaaa atttcaactc attcattcat cagtgaagga    60
gagatgtcca cgacagtgaa cgcatctgcc gatcaaaatc ggaatcttcc tacctaccaa   120
gtgcctaata gtagggacac aatgaatgcg gtagaaacat ctgccgttgc tgtgaggaat   180
aaaatcaaat caccgcacag agcggagagt gatggaggca gagctggcct ctttcacttc   240
ctcccttcga ctgtgataac cagctcatta acttgtagtg gagatccgtc ctacacgcta   300
cagggcttga agcaaaagc tgtcggttca actgatagcg attgttgcga tgaaaaaaga   360
atgatgaggc aagaagcctt gaccctagga tcggttgaca ttggtgctca ggataagtct   420
tctactacta ataattgttc tactattaat gataagcata ggattaagtc cgttgatact   480
actagttgta atgctaataa tgtgacgacg aacaatgcgg aaaacattcc ttcaaatgag   540
tggatagcaa ttttaaatac cacgacaaag ccttattcct caggtgattt acttcagggt   600
aactctaagc taaatcaccg cttaacgaat tccccgttaa actcctttca agactgtgat   660
gttattcgag actaccactt gaggtggaac atcctgccaa cttgtcgatt ggtgggtggt   720
ggggagagtt cgcttgcttc agcaacctcc accaactcgg gctggggaac gaacaacaac   780
aactcaggat cgagcgcccc accaagtgga tggagtgcac cgaccaatgc tgctcagcca   840
ccaccaacat cgactgcttc aggacctcct gccaactgga atagcagcaa cagcaattcc   900
cccaactcat cctcgcaatc tcagtcacaa aaccgtcagc caccggcaaa taatgctagt   960
caaggaacca ataatctgca aaacaatgct tctaaagcaa acccagcgat gagtaccagt  1020
agcaacaatc agcgccagtc aactagccag ccacctccgg ccacttctca agccaatagt  1080
accacatctt gggcacaggc tgctggcaag aaccttccca acgcaccacc taccacaact  1140
cctgcaccac ccatgacttc aacagcatcg accaccaaca acaactcgac gaagcaacag  1200
ttggagcagc tcaactctat gcgtgaagcc ctcttcagtc aggatggttg gggaggacaa  1260
catgtgaacc aagacagtgg ttgggatgtc tccccttcac cagaaccagt tgctaaagat  1320
caaaccggtg caacagtacc tgcatggaag ccaaatataa ataatggaac tgagcttttgg  1380
gaagccaact tgcgcagtgg cggtcagcct gcagctccac cgcaacccaa aacaccatgg  1440
ggccatactc ccacgactaa tattgtggc acgtggggaa aaagatgatga tgtcagtagc  1500
gaagcgacca atgtctggac tggagttcct ccaaacaatc aaccgcaatg gacaggcggc  1560
cccaacaatc ccatgtggcc aggtggagac aaaaaaggta gtgagtgggg tggaaacaat  1620
gccggttggc cgtatgaccc ctcccgcggt cttgctccaa aagttgatcc aagagatcaa  1680
catcgtatgg ctgtagctga tcacagaggc atggtgctg atgataagat tggtttgatg  1740
agaggagatc ctcgtggaat aagtgggcgc ctgaatggag ctggtggtgc tgatcctgct  1800
atgtggggtc ctgctcctcc gccacaacaa ccaccagctc cccatcatcc cccgcctgga  1860
ccacctcctg gacctggtca accacccaac aaaattttac caccagctct agctggcgta  1920
aaccattgga ctggtcccaa ctctaatgat atgaacattgg cgctggtgg aggaaaaccc  1980
aatggctggg acgaaccctc tccacctgct caaagacgga acatgccaaa catgcctggt  2040
tatgacgacg gtcagctctc atgggggaaat caaggtaaca ataaagtcac tcattggaaa  2100
gaaatgccaa atcctaatat ggctcatgga atgcccggcc ctgccatccc tcaaaataga  2160
atgcctggaa atgttaccaa catgaaacct gatccgtctt cttggggtca cccgactaga  2220
aacggaggat ggggcgatgg atctgctaac cctggaagtg gcccagactc aagcgtgcct  2280
tggggtgatg acaaaattgc gggtaactgg aacgagccac cgataccatc tggttgggct  2340
ggtacgggctc cgccgaagaa tgcacccgga ccgtggattg atggtgatgt tgacccatca  2400
aattgggccc atcctcccaa gcagggtcca aagccgttga ctaaagatat catttggtct  2460
agcaagcagt tcagaattct tgctgatatg ggtttcaaga aagatgatat tgaaaacgca  2520
ttgcgtgtca gcaacatggt tctgaagat gctctagaaa tgctgaaccc agcgcgaaat  2580
gtgggaggtc ctaatgctcc tgatctctgg cgtcccgacg ctgccgctcc atttgaccca  2640
acgcaattcc ctccctctca gcctcgcttt ccgcagcaga tgccttttcgc tcctccgaca  2700
ggtgtcgctc cgtcggttcc cccacctccc catcagaagt tgctctctca gccaccgcca  2760
tccacagccg tcagcaacc accacattc aatcaatctt caagaggagg gaactcgagc  2820
tatcaaccga ctcctcagca gcttcgtgtt tggttcagc aaatcacaat ggcagttcaa  2880
gctgggtatc ttaatcagca gatattgaat cagcccttgg ctcctcagac tcttctcctt  2940
ttaaatcagt tacttcaaca tatcaagtcg cttcaacaac ttatccagca gagaaatcta  3000
catgccagca gcaacccctct tgggaagagc aacaactcag cattcatgca ccttacagct  3060
caaatcacca aaaccaagaa acatatcgcc gggcttcaga acgacatagt aattcagcaa  3120
gcgcagtata tcaaaaacca gataccatca cagcagcatc agcagcaaca ccaccttgca  3180
tcaggcaata atcagtcaca aggtaactga ggtggtggga gtagcaatga tttcttcaac  3240
aagaatcaag cacaggatct cttggcagct cttcaaacca atttcacaga cttgaacatt  3300
aataaagaac cattgtcaag tggagcaggt ttccaacacc agcaatcacg tttgaatcaa  3360
tggaagttac catctctgga caaggagggt gaagtcggtg aagacttcag ccgtgcccca  3420
ggaaccacct ctaaatctgg aggctctacg tctcccacat taatcctct gctgggccca  3480
gacgggcctt ggtcatcaag tgtttcgaat gcaaacagca ctggttggcc cgattctgag  3540
aaaagactgg cttcatcaca ggccaactcc tcatctgcgt ttactgacct tgtgcctgag  3600
tttgagcctg gaaaccgtg gaaggcagt gtattgaaaa gcattgaaga tgaccctagc  3660
atcaccccctg atcagtcgt acgatctccc ctcagcctgg cctcaatcaa agactcagaa  3720
atatttagct ctagtaagac ttcgccaaac agcaccaaca actccgcctc tgacaactta  3780
cctctacctc cgctgtctct gtcgtcatca acttggagct tcaatccctc ttcaactgca  3840
ccttcttctt ttactggacc tcttgccaaa ttgggcacta ctggtaaaac aaccagttgg  3900
ggagatgctc agcaccaaac tgtagttaca tgcgaactgt ggggcgcaac gaaatcagga  3960
ggtcctcccc caggtctctc ctccaagact ggctctgctc aaaactcagg ttcaagtagc  4020
aatggctgga ctgctggctc caattggagt agtggcgctc attccggctc atcctctcag  4080
tggccctcat cttcatcatg gcttttactc cgaaatttga ctgctcagat cgatggttca  4140
acattaaaaa cgctttgttg tcaacacggt cctctgcaaa acttccattt gtacctgaaa  4200
catgggattg cccttgctaa atactcaaca aaagaagagg ctgtgaaggc tcaaggtgct  4260
```

```
ttgaacaatt gcgtgttagg gaacacgaca atattcgcag aatctccggc cgagtcagaa    4320
gtgcattcat tacttcaaca cctcggccag caaggagggt ccaacagtgg ctggaaccgt    4380
cctacggggg gagccccgaa acctgcaggt acaactgata cttggagctc gggttggccg    4440
tcaaactcac cttcaagtag cttgtggggt gctcctcctt tggacgagca tcgctcaacc    4500
ccatctttga attctttctt acctggtgat cttttgggtg gtgaatcaat gtaa          4554

SEQ ID NO: 2           moltype = DNA  length = 28
FEATURE                Location/Qualifiers
source                 1..28
                       mol_type = other DNA
                       organism = synthetic construct
SEQUENCE: 2
cgagctcgct tcttactccg tggcaacc                                       28

SEQ ID NO: 3           moltype = DNA  length = 28
FEATURE                Location/Qualifiers
source                 1..28
                       mol_type = other DNA
                       organism = synthetic construct
SEQUENCE: 3
cctcgaggtg acatcattgc tcctgcat                                       28
```